(12) United States Patent
Adams et al.

(10) Patent No.: US 10,576,091 B2
(45) Date of Patent: *Mar. 3, 2020

(54) TOMATIDINE, ANALOGS THEREOF, COMPOSITIONS COMPRISING SAME, AND USES FOR SAME

(71) Applicants: UNIVERSITY OF IOWA RESEARCH FOUNDATION, Iowa City, IA (US); THE UNITED STATES GOVERNMENT AS REPRESENTED BY THE DEPARTMENT OF VETERANS AFFAIRS, Washington, DC (US)

(72) Inventors: Christopher M. Adams, Iowa City, IA (US); Michael C. Dyle, Iowa City, IA (US); Michael Welsh, Riverside, IA (US)

(73) Assignees: UNIVERSITY OF IOWA RESEARCH FOUNDATION, Iowa City, IA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,184

(22) Filed: Jun. 8, 2018

(65) Prior Publication Data

US 2018/0289725 A1  Oct. 11, 2018

Related U.S. Application Data

(63) Continuation of application No. 14/978,886, filed on Dec. 22, 2015, now Pat. No. 10,022,386, which is a continuation of application No. 14/612,636, filed on Feb. 3, 2015, now Pat. No. 9,254,295, which is a continuation of application No. PCT/US2013/053423, filed on Aug. 2, 2013.

(60) Provisional application No. 61/730,496, filed on Nov. 27, 2012, provisional application No. 61/679,432, filed on Aug. 3, 2012.

(51) Int. Cl.

| | |
|---|---|
| *A61K 31/58* | (2006.01) |
| *C07J 53/00* | (2006.01) |
| *A23K 20/121* | (2016.01) |
| *A61K 45/06* | (2006.01) |
| *C12Q 1/6883* | (2018.01) |
| *A23L 33/10* | (2016.01) |
| *A61P 21/00* | (2006.01) |

(52) U.S. Cl.
CPC ............ *A61K 31/58* (2013.01); *A23K 20/121* (2016.05); *A23L 33/10* (2016.08); *A61K 45/06* (2013.01); *A61P 21/00* (2018.01); *C07J 53/00* (2013.01); *C12Q 1/6883* (2013.01); *A23V 2002/00* (2013.01); *C12Q 2600/136* (2013.01); *C12Q 2600/158* (2013.01)

(58) Field of Classification Search
CPC ................................ A61P 21/00; A61K 31/58
See application file for complete search history.

(56) References Cited

U.S. PATENT DOCUMENTS

| | | | |
|---|---|---|---|
| 9,254,295 B2 | 2/2016 | Adams et al. | |
| 9,295,664 B2 | 3/2016 | Adams et al. | |
| 10,022,386 B2 | 7/2018 | Adams et al. | |
| 2006/0062863 A1 | 3/2006 | Ghosal | |
| 2009/0143279 A1 | 6/2009 | Mootha et al. | |
| 2010/0112030 A1 | 5/2010 | Parhami et al. | |
| 2010/0204121 A1 | 8/2010 | Romero et al. | |
| 2011/0008333 A1 | 1/2011 | Dudek et al. | |
| 2012/0177730 A1 | 7/2012 | Baron et al. | |
| 2016/0243132 A1 | 8/2016 | Adams et al. | |

FOREIGN PATENT DOCUMENTS

| | | |
|---|---|---|
| EP | 0020029 A1 | 12/1980 |
| EP | 0774255 B1 | 10/2001 |
| JP | 56154500 A | 11/1981 |
| WO | 2006007910 A1 | 1/2006 |
| WO | 2006036638 A1 | 4/2006 |
| WO | WO2011146768 A1 | 11/2011 |
| WO | WO2012033422 A1 | 3/2012 |
| WO | WO2012170546 A1 | 12/2012 |
| WO | 2013078372 A1 | 5/2013 |
| WO | WO2013078372 A1 | 5/2013 |

OTHER PUBLICATIONS

International Search Report for PCT/US2013/053423 dated Dec. 19, 2013 (2 pages).

Chiu, et al., "Tomatidine Inhibits iNOS and COX-2 through Suppression of NF-kB and JNK Pathways in LPS-Stimulated Mouse Macrophages", FEBS Letters 582 (2008) 2407-2412, Jun. 9, 2008, (6 pages).

Choi, et al., Structure-Activity Relationships of Alpha-, Beta(1)-, Gamma-, and Delta-Tomatine and Tomatidine Against Human Breast (MDA-MB-231), Gastric (Kato-III), and Prostate (PC3) Cancer Cells, Journal of Agricultural and Food Chemistry, Apr. 6, 2012, (9 pages).

Kessar, et al., "Synthetic Studies in Steroidal Sapogenins and Alkaloids—X", Tetrahedron, vol. 22, Mar. 17, 1971, (7 pages).

Fujiwara, et al., Tomatidine, a Tomato Sapogenol, Ameliorates Hyperlipidemia and Atherosclerosis in ApoE-Deficient Mice by Inhibiting Acyl-CoA:cholesterol Acyl-transferase (ACAT), ACS Publications, Journal of Agricultural and Food Chemistry, Dec. 30, 2011 (8 pages).

(Continued)

*Primary Examiner* — Theodore R. West
(74) *Attorney, Agent, or Firm* — Heslin Rothenberg Farley & Mesiti P.C.

(57) ABSTRACT

In one aspect, the invention relates to methods for promoting muscle hypertrophy or decreasing adiposity by providing to an animal in need thereof an effective amount of a compound. This abstract is intended as a scanning tool for purposes of searching in the particular art and is not intended to be limiting of the present invention.

25 Claims, 12 Drawing Sheets

(56) References Cited

OTHER PUBLICATIONS

Friedman, M., et al., "α-Tomatine Content in Tomato and Tomato Products Determined by HPLC with Pulsed Amperometric Detection", J. Agric. Food Chem., vol. 43, No. 6, pp. 1507-1511 (1995).

Koh, E., et al., "A long-term comparison of the influence of organic and conventional crop management practices on the content of the glycoalkaloid α-tomatine in tomatoes", J. Sci. Food Agric., vol. 93, pp. 1537-1542 (2013).

Rick, C.M., et al., "High α-tomatine content in ripe fruit of Andean *Lycopersicon esculentum* var. *cerasiforme*: Developmental and genetic aspects", Proc. Natl. Acad. Sci. USA, vol. 91, pp. 12877-12881 (1994).

International Search Report for PCT/US2013/053423 dated Dec. 19, 2013.

Fugiwara, Y., et al., Tomatidine, a Tomato Sapogenol, Ameliorates Hyperlipidemia and Atherosclerosis in ApoE-Deficient Mice by Inhibiting Acyl-CoA: cholesterol Acyl-transferase (ACAT), American Chemical Society Publications, "Journal of Agricultural and Food Chemistry", vol. 60, pp. 2472-2479 (2012).

Friedman, M., et al., "Effect of feeding solanidine, solasodine and tomatidine to non-pregnant and pregnant mice", Food and Chemical Toxicology, vol. 41, pp. 61-71 (2003).

Qiaoxia Xu et.al., "Study on Separation and Purification of Tomatidine from Green Tomato", *Agricultural product processing-test research*, Mar. 2010, pp. 71-75.

Human Muscle Atrophy Signature-1

| Conserved Effects of Fasting on Human and Mouse Skeletal Muscle ||
|---|---|
| Induced mRNAs | Repressed mRNAs |
| ABCA1 | ACACA |
| ACOX1 | BPGM |
| ADPGK | CACNB1 |
| CALCOCO1 | CASQ1 |
| CAT | CNNM4 |
| CITED2 | DNMT3A |
| CPT1A | FEZ2 |
| GABARAPL1 | GAS2 |
| HERPUD1 | GRTP1 |
| HMOX1 | HSPH1 |
| IGF1R | JTB |
| INSR | MRPS15 |
| MED13L | MTSS1 |
| MYO5A | NEO1 |
| NBR1 | NFYA |
| NOX4 | P4HA2 |
| PDK4 | PBX1 |
| PPAP2B | PDE7B |
| RORA | PMP22 |
| SESN1 | PGC-1α |
| SFRS8 | PTX3 |
| SLC38A2 | SLC4A4 |
| SRRM2 | SPINT2 |
| SUPT6H | ST8SIA5 |
| TULP3 | SUV39H2 |
| TXNIP | TFRC |
| UBE4A | TGFB2 |
| UCP2 | TSPAN13 |
| UCP3 | TTLL1 |
| XPO4 | VEGFA |
| ZFAND5 | WDR1 |
|  | ZNF280B |

FIG. 16

Human Muscle Atrophy Signature-2

| Conserved Effects of Fasting and SCI on Human Skeletal Muscle ||
|---|---|
| Induced mRNAs | Repressed mRNAs |
| CAV3 | CMAS |
| CTDSP2 | GUCY1B3 |
| CUGBP2 | HSPB7 |
| IGF1R | MRPS15 |
| IRS2 | PDE7B |
| KLF11 | PFDN6 |
| MLL | PGC-1α |
| NOX4 | SLC16A1 |
| NPC2 | TSPAN13 |
| NUPR1 | TTLL1 |
| OR1D4 | VEGFA |
| RHOBTB1 | VLDLR |
| SUPT6H | ZNF280B |
| TSPAN8 | ZNF32 |
| ZNF682 |  |

FIG. 17

TOMATIDINE, ANALOGS THEREOF, COMPOSITIONS COMPRISING SAME, AND USES FOR SAME

CROSS-REFERENCE TO RELATED APPLICATIONS

This Application is a continuation of U.S. application Ser. No. 14/978,886, filed Dec. 22, 2015, which is a continuation of U.S. application Ser. No. 14/612,636, filed Feb. 3, 2015 (now U.S. Pat. No. 9,254,295, issued Feb. 9, 2016), which is a continuation of PCT/US2013/053423, filed Aug. 2, 2013, which claims the benefit of U.S. Provisional Application No. 61/679,432, filed Aug. 3, 2012, and U.S. Provisional Application No. 61/730,496, filed Nov. 27, 2012. The entire contents of each of the prior applications are hereby incorporated by reference herein.

STATEMENT REGARDING FEDERALLY SPONSORED RESEARCH

This invention was made with government support under grant IBX000976A awarded by the Department of Veterans Affairs Biomedical Laboratory Research & Development Service and grant 1R01AR059115-01 awarded by the National Institutes of Health and National Institute of Arthritis and Musculoskeletal and Skin Diseases (NIH/NIAMS). The United States government has certain rights in the invention.

BACKGROUND

Skeletal muscle atrophy is characteristic of starvation and a common effect of aging. It is also a nearly universal consequence of severe human illnesses, including cancer, chronic renal failure, congestive heart failure, chronic respiratory disease, insulin deficiency, acute critical illness, chronic infections such as HIV/AIDS, muscle denervation, and many other medical and surgical conditions that limit muscle use. However, medical therapies to prevent or reverse skeletal muscle atrophy in human patients do not exist. As a result, millions of individuals suffer sequelae of muscle atrophy, including weakness, falls, fractures, opportunistic respiratory infections, and loss of independence. The burden that skeletal muscle atrophy places on individuals, their families, and society in general, is tremendous.

The pathogenesis of skeletal muscle atrophy is not well understood. Nevertheless, important advances have been made. For example, it has been described previously that insulin/IGF 1 signaling promotes muscle hypertrophy and inhibits muscle atrophy, but is reduced by atrophy-inducing stresses such as fasting or muscle denervation (Bodine S C, et al. (2001) *Nat Cell Biol* 3(11):1014-1019; Sandri M, et al. (2004) *Cell* 117(3):399-4121; Stitt T N, et al. (2004) *Mol Cell* 14(3):395-403; Hu Z, et al. (2009) *The Journal of clinical investigation* 119(10):3059-3069; Dobrowolny G, et al. (2005) *The Journal of cell biology* 168(2): 193-199; Kandarian S C & Jackman R W (2006) *Muscle & nerve* 33(2): 155-165; Hirose M, et al. (2001) *Metabolism: clinical and experimental* 50(2):216-222; Pallafacchina G, et al. (2002) *Proceedings of the National Academy of Sciences of the United States of America* 99(14):9213-9218). The hypertrophic and anti-atrophic effects of insulin/IGF 1 signaling are mediated at least in part through increased activity of phosphoinositide 3-kinase (PI3K) and its downstream effectors, including Akt and mammalian target of rapamycin complex 1 (mTORC1) Sandri M (2008) *Physiology* (Bethesda) 23:160-170; Glass D J (2005) *The international journal of biochemistry & cell biology* 37(10): 1974-1984).

Another important advance came from microarray studies of atrophying rodent muscle (Lecker S H, et al. (2004) *Faseb J* 18(1):39-51; Sacheck J M, et al. (2007) *Faseb J* 21(1): 140-155; Jagoe R T, et al. *Faseb J* 16(13): 1697-1712). Those studies showed that several seemingly disparate atrophy-inducing stresses (including fasting, muscle denervation and severe systemic illness) generated many common changes in skeletal muscle mRNA expression. Some of those atrophy-associated changes promote muscle atrophy in mice; these include induction of the mRNAs encoding atroginl/MAFbx and MuRF1 (two E3 ubiquitin ligases that catalyze proteolytic events), and repression of the mRNA encoding PGC-1α (a transcriptional co-activator that inhibits muscle atrophy) (Sandri M, et al. (2006) *Proceedings of the National Academy of Sciences of the United States of America* 103(44): 16260-16265; Wenz T, et al. *Proceedings of the National Academy of Sciences of the United States of America* 106(48):20405-20410; Bodine S C, et al. (2001) *Science* (New York, N.Y. 294(5547): 1704-1708; Lagirand-Cantaloube J, et al. (2008) *The EMBO journal* 27(8): 1266-1276; Cohen S, et al. (2009) *The Journal of cell biology* 185(6):1083-1095; Adams V, et al. (2008) *Journal of molecular biology* 384(1):48-59). However, the roles of many other mRNAs that are increased or decreased in atrophying rodent muscle are not yet defined. Data on the mechanisms of human muscle atrophy are even more limited, although atrogin-1 and MuRF1 are likely to be involved (Leger B, et al. (2006) *Faseb J* 20(3):583-585; Doucet M, et al. (2007) *American journal of respiratory and critical care medicine* 176(3):261-269; Levine S, et al. (2008) *The New England journal of medicine* 358(13): 1327-1335). It is therefore beneficial to have compounds that can increase skeletal muscle, muscle hypertrophy. Therefore, compounds that can promote muscle hypertrophy are desired.

Furthermore, it is well known that obesity is a major problem in today's society. Millions of dollars are spent each year in treating diseases directly linked to people being over weight. These problems can be caused by a high adiposity. Therefore, compounds that can decrease adiposity are desired.

Tomatidine is a naturally occurring steroidal alkaloid that is the aglycone form of α-tomatine, an abundant glycoalkaloid in tomato plants and tomatoes. In tomatoes, α-tomatine mediates plant defense against fungi, bacteria, viruses and predatory insects (Koh E et al. (2013) *J. Sci. Food Agric.* 93: 1537-1542). When consumed by animals, α-tomatine is hydrolyzed by stomach acid and intestinal bacteria to tomatidine, which is absorbed by the gut (Friedman M et al (2003) *Food Chem. Toxicol.* 41: 61-71). Tomatidine appears to have a favorable safety profile based on several studies: 1) human consumption of indigenous variants of tomatoes with very high concentrations of □ α-tomatine (up to 0.05% (w/w) of dry tomato weight) appears to cause no adverse effects (Koh E et al. (2013) *J. Sci. Food Agric.* 93: 1537-1542; Rick C et al. (1994) *Proc. Natl. Acad. Sci. U.S.A.* 91: 12877-12881); 2 α-tomatine content is twice as high in organically grown tomatoes compared to conventionally grown tomatoes (Koh E et al. (2013) *J. Sci. Food Agric.* 93: 1537-1542); and 3) in pregnant and non-pregant mice, dietary supplementation with 0.1% (w/w) tomatidine produces no adverse effects (Friedman M et al (2003) *Food Chem. Toxicol.* 41: 61-71). Moreover, in mouse models, tomatidine possesses anti-hyperlipidemic and anti-atherosclerotic effects without evidence of toxicity (Fujiwara Y et al. (2012) *J. Agric. Food Chem.* 60: 2472-2479). Prior to this research, the ability of tomatidine to promote skeletal muscle hypertrophy, increase muscle strength, increase exercise capacity, and decrease adiposity was unknown.

Despite advances in understanding the physiology and pathophysiology of muscle atrophy, there is still a scarcity of compounds that are both potent, efficacious, and selective modulators of muscle growth and also effective in the treatment of muscle atrophy associated and diseases in which the muscle atrophy or the need to increase muscle mass is involved. There is also a need for compounds that can decrease adiposity. There is also a need for compounds that can promote muscle hypertrophy. These needs and other needs are satisfied by the present invention.

SUMMARY

In accordance with the purpose(s) of the invention, as embodied and broadly described herein, the invention, in one aspect, relates to compounds useful in methods to treat muscle atrophy, promote muscle hypertrophy, and decrease adiposity. The compounds can be selected from tomatidine and analogs. Tomatidine and tomatidine analogs are used interchangeably herein.

Tomatidine and analogs can have the structure:

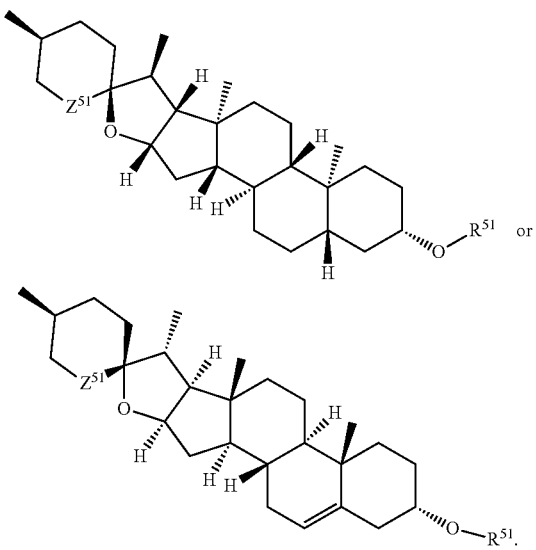

The disclosed compounds can promote muscle hypertrophy when administered in an effective amount to an animal, such as a mammal, fish or bird. For example, human.

The disclosed compounds can decrease adiposity when administered in an effective amount to an animal, such as a mammal, fish or bird. For example, human.

The disclosed compounds can also treat muscle atrophy when administered in an effective amount to an animal, such as a mammal, fish or bird. For example, human.

The disclosed compounds can also promote muscle health, promote normal muscle function, and/or promote healthy aging muscles by providing to a subject in need thereof an effective amount of a disclosed compound.

Also disclosed herein are pharmaceutical compositions comprising compounds used in the methods. Also disclosed herein are kits comprising compounds used in the methods.

Also disclosed are methods for manufacturing a medicament associated with muscle atrophy or the need to promote muscle health, promote normal muscle function, and/or promote healthy aging muscles comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with muscle atrophy or the need to promote muscle health, promote normal muscle function, and/or promote healthy aging muscles.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 16 is a listing of the induced and repressed mRNAs associated with human muscle atrophy signature-1.

FIG. 17 is a listing of the induced and repressed mRNAs associated with human muscle atrophy signature-2.

Figure 1:
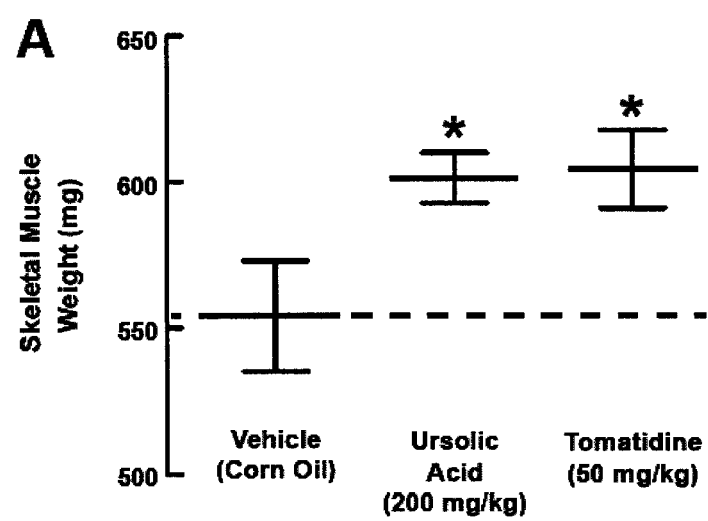
FIG. 1 is a graph of mouse skeletal muscle weight for control, ursolic acid at 200 mg/kg and tomatidine at 50 mg/kg.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "muscle atrophy signature-1" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-1 comprises the induced and repressed mRNAs described in FIG. 16.

As used herein, the term "muscle atrophy signature-2" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-2 comprises the induced and repressed mRNAs described in FIG. 17.

As used herein, the term "subject" refers to the target of administration, e.g. an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for promoting muscle health prior to the administering step. In some aspects of the disclosed method, the subject has been diagnosed with a need for promoting muscle health prior, promote normal muscle function, and/or promote healthy aging muscles to the administering step.

As used herein, the term "treatment" refers to the medical management of a patient with the intent to cure, ameliorate, stabilize, or prevent a disease, pathological condition, or disorder. This term includes the use for astetic and self-improvement purposes, for example, such uses include, but are not limited to, the administration of the disclosed compound in nutraceuticals, medicinal food, energy bar, energy drink, sports drink, protein bar, tea, coffee, milk, milk products, cereal, oatmeal, infant formulas, supplements (such as multivitamins). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, fish, bird, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a muscle atrophy disorder" means having been subjected to a physical examination by a person of skill, for example, a physician, and found to have a condition that can be diagnosed or treated by a compound or composition that can promote muscle health, promote normal muscle function, and/or promote healthy aging muscles. As a further example, "diagnosed with a need for promoting muscle health" refers to having been subjected to a physical examination by a person of skill, for example, a physician, and found to have a condition characterized by muscle atrophy or other disease wherein promoting muscle health, promoting normal muscle function, and/or promoting healthy aging muscles would be beneficial to the subject. Such a diagnosis can be in reference to a disorder, such as muscle atrophy, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to muscle atrophy) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the a gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula AO$^1$A$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$—C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR*, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR*, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

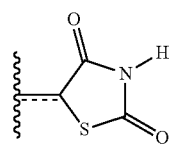

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

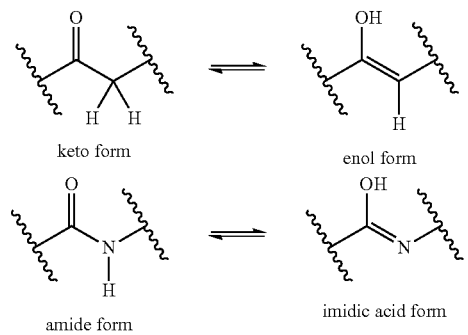

keto form     enol form amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

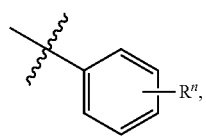

which is understood to be equivalent to a formula:

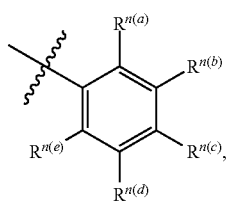

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in methods to promote muscle hypertrophy by providing to a subject in need thereof an effective amount of a compound or an analog thereof selected from among the compounds described herein. In another aspect, the invention relates to compounds useful in methods to decrease adiposity by providing to a subject in need thereof an effective amount of a compound or an analog thereof selected from among the compounds described herein. In another aspect, the invention relates to compounds useful in methods to inhibit muscle atrophy by providing to a subject in need thereof an effective amount of a compound or an analog thereof selected from among the compounds described herein, and pharmaceutical compositions comprising compounds used in the methods. In a further aspect, the invention relates to compounds identified using muscle atrophy signature-1, muscle atrophy signature-2, or both muscle atrophy signatures. In a further aspect, the invention relates to compounds useful in methods to modulate muscle health, methods to inhibit muscle atrophy, methods to increase anabolic signaling, methods to increase protein synthesis, methods to increase mitochondria, methods to increase muscle force generation, methods to increase muscle strength, methods to increase exercise capacity, methods to increase the growth of cultured skeletal muscle cells, methods to reduce body fat, methods to reduce blood glucose, methods to reduce blood triglycerides, methods to reduce blood cholesterol, methods to reduce obesity, methods to reduce fatty liver disease, and methods to reduce diabetes, and pharmaceutical compositions comprising compounds used in the methods.

In one aspect, the compounds of the invention are useful in the treatment of muscle disorders. In a further aspect, the muscle disorder can be skeletal muscle atrophy secondary to malnutrition, bed rest, neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome, growth hormone deficiency, IGF-I deficiency, androgen deficiency, estrogen deficiency, and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Tomatidine and Analogs

In one aspect, the compound can be a tomatidine analog.

In one aspect, the tomatidine analog has a structure represented by a formula:

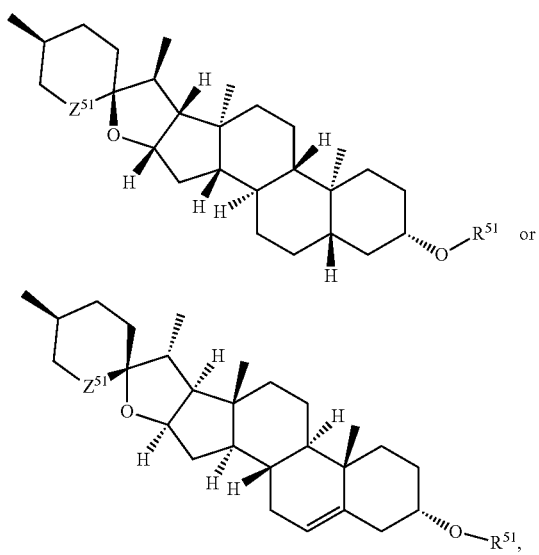

wherein $R^{51}$ is selected from H, C1-C6 alkyl, $COR^{53}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{53}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $Z^{51}$ is selected from O, S, and $NR^{54}$;

wherein $R^{54}$ is selected from H, C1-C6 alkyl, $COR^{55}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{55}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or a stereoisomer, tautomer, solvate, or pharmaceutically acceptable salt thereof.

In one aspect, $R^{51}$ is selected from H, C1-C6 alkyl and $COR^{53}$, wherein $R^{53}$ is C1-C6 alkyl. In another aspect, $R^{51}$ is H. In another aspect, $Z^{51}$ is $NR^{54}$. In another aspect, $Z^{51}$ is $NR^{54}$, wherein $R^{54}$ is selected from H, C1-C6 alkyl, and $COR^{55}$, wherein $R^{55}$ is C1-C6 alkyl.

In another aspect, $R^{51}$ is selected from H, C1-C6 alkyl and $COR^{53}$, wherein $R^{53}$ is C1-C6 alkyl; and $Z^{51}$ is $NR^{54}$, wherein $R^{54}$ is selected from H, C1-C6 alkyl, and $COR^{55}$, wherein $R^{55}$ is C1-C6 alkyl. In another aspect, $R^{51}$ and $R^{54}$ are identical.

In another aspect, the structure is represented by the formula:

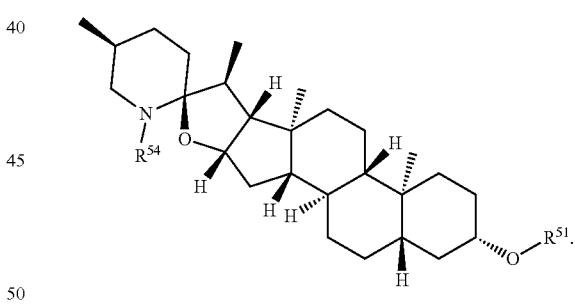

In another aspect, the structure is represented by the formula:

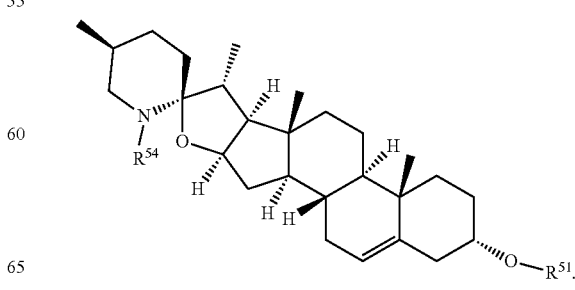

In another aspect, the formula has the structure:

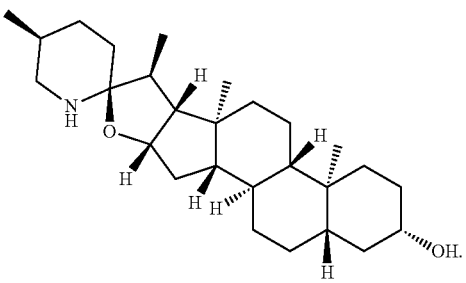 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

2. Dehydrotomatidine and Analogs

In various aspects, the compound can be a dehydrotomatidine analog.

In one aspect, the dehydrotomatidine analog has a structure represented by a formula:

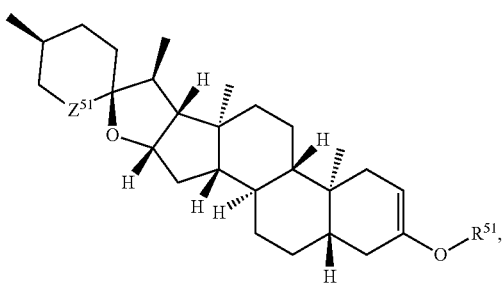

wherein $R^{51}$ is selected from H, C1-C6 alkyl, $COR^{53}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{53}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $Z^{51}$ is selected from O, S, and $NR^{54}$;

wherein $R^{54}$ is selected from H, C1-C6 alkyl, $COR^{55}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{55}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or a stereoisomer, tautomer, solvate, or pharmaceutically acceptable salt thereof.

In one aspect, $R^{51}$ is selected from H, C1-C6 alkyl and $COR^{53}$, wherein $R^{53}$ is C1-C6 alkyl. In another aspect, $R^{51}$ is H. In another aspect, $Z^{51}$ is $NR^{54}$. In another aspect, $Z^{51}$ is $NR^{54}$, wherein $R^{54}$ is selected from H, C1-C6 alkyl, and $COR^{55}$, wherein $R^{55}$ is C1-C6 alkyl.

In another aspect, $R^{51}$ is selected from H, C1-C6 alkyl and $COR^{53}$, wherein $R^{53}$ is C1-C6 alkyl; and $Z^{51}$ is $NR^{54}$, wherein $R^{54}$ is selected from H, C1-C6 alkyl, and $COR^{55}$, wherein $R^{55}$ is C1-C6 alkyl. In another aspect, $R^{51}$ and $R^{54}$ are identical.

In another. In another aspect, the structure is represented by the formula:

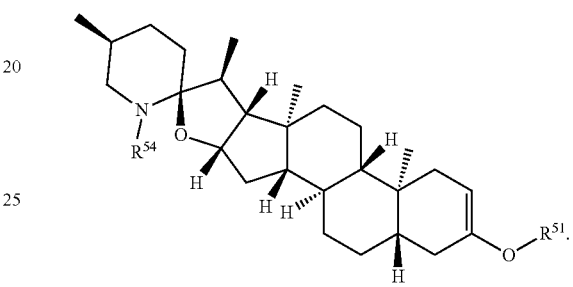

In another aspect, the structure is represented by the formula:

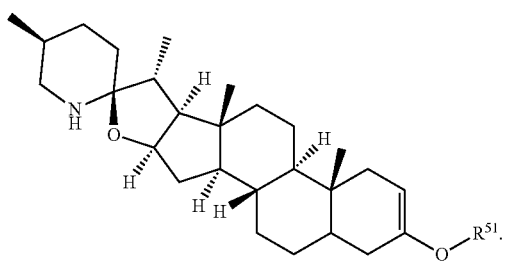

In another aspect, the formula has the structure:

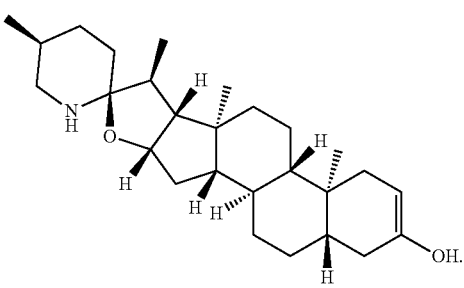 [SMILES: C[C@H]1CC[C@]2(NC1)O[C@H]1C[C@H]3[C@@H]4CC[C@H]5CC(O)=CC[C@]5(C)[C@H]4CC[C@]3(C)[C@H]1[C@@H]2C]

3. Prodrugs

In various aspects, the compounds further comprise prodrugs thereof, and pharmaceutically acceptable salts of said compounds. In a further aspect, the compounds further comprise prodrugs in the form of tomatine analogs.

In one aspect, the tomatine analog has a structure represented by a formula:

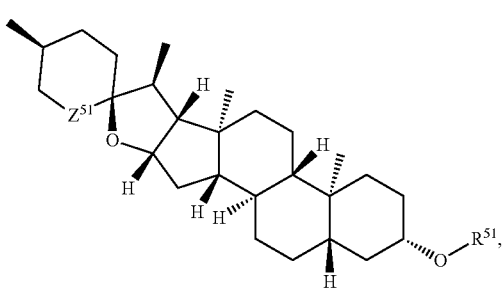

wherein $R^{51}$ is selected from H, C1-C6 alkyl, $COR^{53}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or wherein $R^{51}$ is selected from a structure:

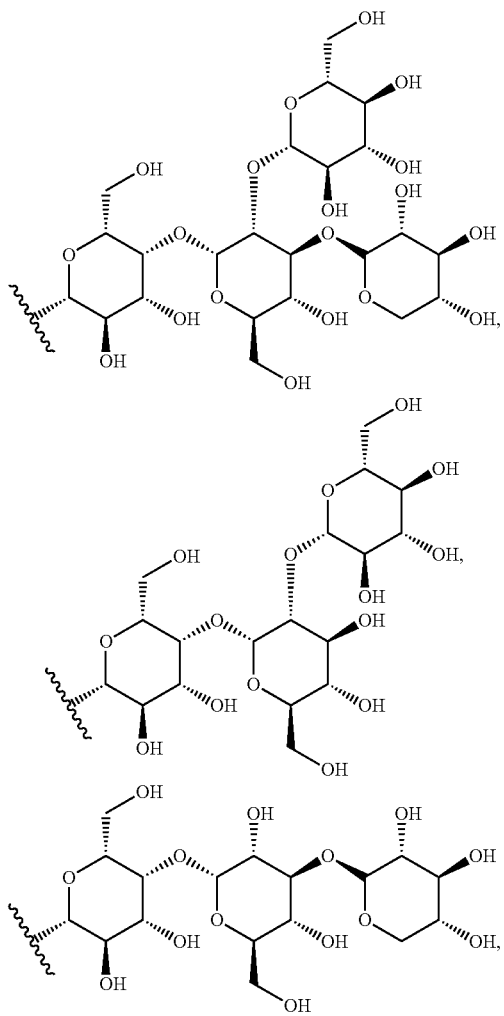

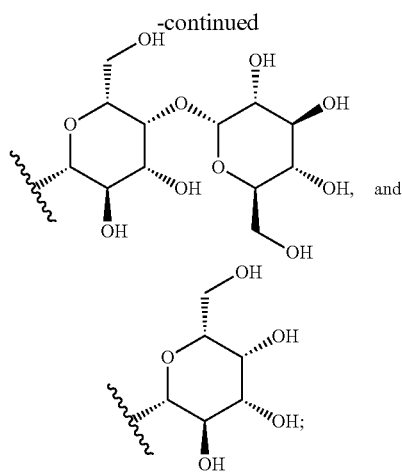

wherein $R^{53}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $Z^{51}$ is selected from O, S, and $NR^{54}$;

wherein $R^{54}$ is selected from H, C1-C6 alkyl, $COR^{55}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{55}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or a stereoisomer, tautomer, solvate, or pharmaceutically acceptable salt thereof.

In another aspect, the structure is represented by the formula:

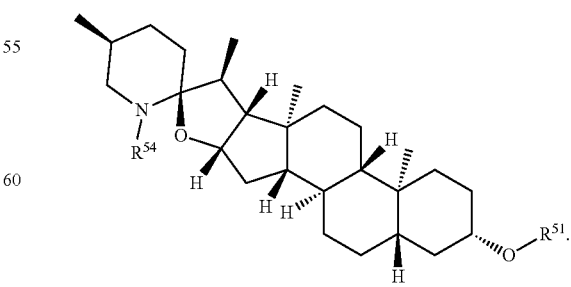

In another aspect, the structure is represented by the formula:

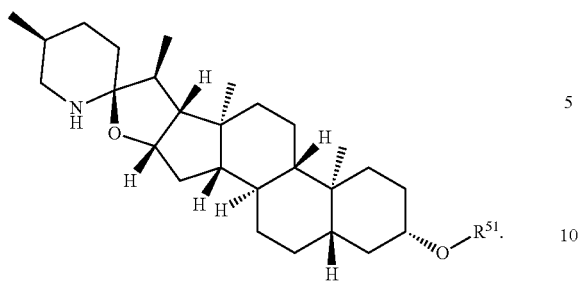
In another aspect, the formula has the structure:
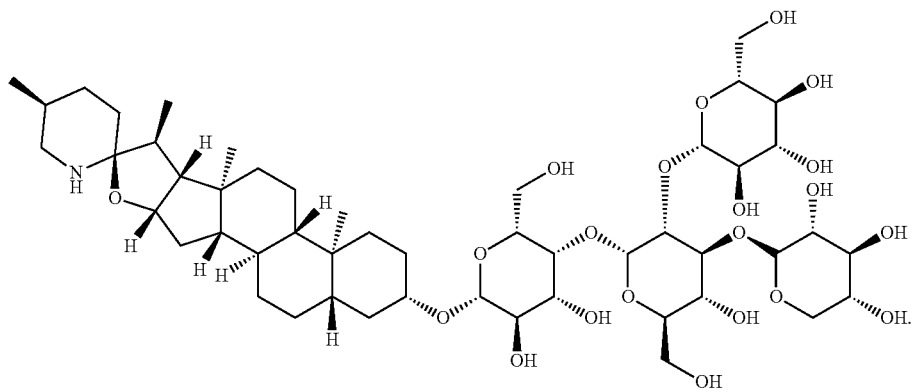
In another aspect, the formula has the structure:
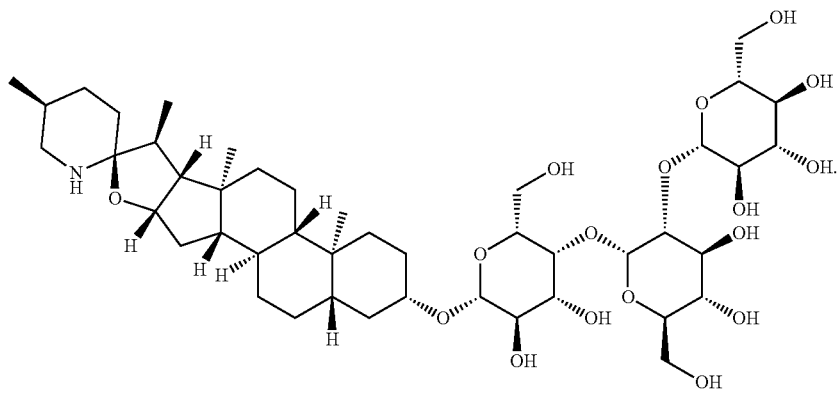 [SMILES: C[C@H]1CC[C@]2(NC1)O[C@H]1C[C@H]3[C@@H]4CC[C@H]5C[C@@H](O[C@@H]6O[C@H](CO)[C@H](O[C@H]7O[C@H](CO)[C@@H](O)[C@H](O)[C@H]7O[C@@H]7O[C@H](CO)[C@@H](O)[C@H](O)[C@H]7O)[C@H](O)[C@H]6O)CC[C@]5(C)[C@H]4CC[C@]3(C)[C@H]1[C@@H]2C]
In another aspect, the formula has the structure:
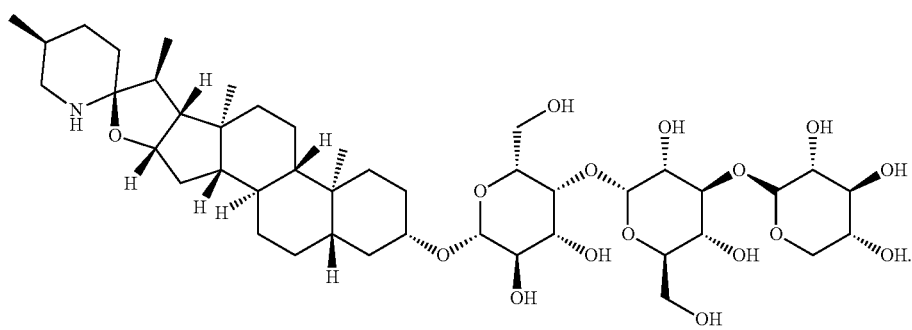

In another aspect, the formula has the structure:

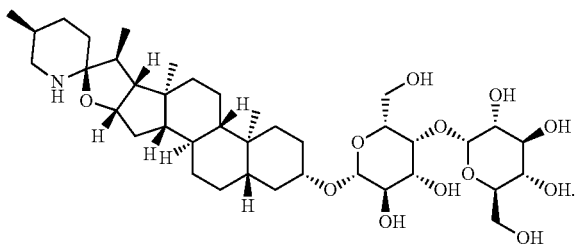 [SMILES: C[C@H]1CC[C@]2(NC1)O[C@H]1C[C@H]3[C@@H]4CC[C@H]5C[C@@H](O[C@@H]6O[C@H](CO)[C@H](O[C@H]7O[C@H](CO)[C@@H](O)[C@H](O)[C@H]7O)[C@H](O)[C@H]6O)CC[C@]5(C)[C@H]4CC[C@]3(C)[C@H]1[C@@H]2C]

In another aspect, the formula has the structure.

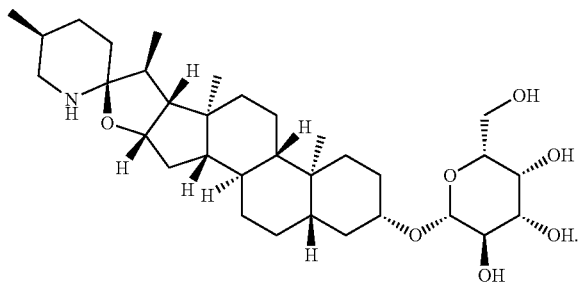 [SMILES: C[C@H]1CC[C@]2(NC1)O[C@H]1C[C@H]3[C@@H]4CC[C@H]5C[C@@H](O[C@@H]6O[C@H](CO)[C@H](O)[C@H](O)[C@H]6O)CC[C@]5(C)[C@H]4CC[C@]3(C)[C@H]1[C@@H]2C]

4. Promotion of Muscle Hypertrophy

In one aspect, the disclosed compounds promote muscle hypertrophy. In a further aspect, the disclosed compounds increase muscle mass in an animal when administered in an effective amount. In a yet further aspect, the disclosed compounds increase muscle hypertrophy. In a yet further aspect, the disclosed compounds increase muscle strength. In a yet further aspect, the disclosed compounds increase cellular protein. The increase in cellular protein can be in vitro or in vivo. For example, the disclosed compounds increase cellular protein in a subject when administered in an effective amount. In a yet further aspect, the disclosed compounds promotes growth of muscle cells. The growth of muscle cells can be in vitro and/or in vivo. In a still further aspect, the animal is a mammal. In a yet further aspect, the mammal is a human. In a further aspect, the mammal is a mouse. In a yet further aspect, the mammal is a rodent. In a yet further aspect, the animal is a fish or a bird.

In a further aspect, the disclosed compounds promote muscle hypertrophy when administered at an oral dose of greater than about 5 mg per day in a human. In a further aspect, the disclosed compounds promote muscle hypertrophy when administered at an oral dose of greater than about 10 mg per day in a human. In a further aspect, the disclosed compounds promote muscle hypertrophy when administered at an oral dose of greater than about 25 mg per day in a human. In a further aspect, the disclosed compounds promote muscle hypertrophy when administered at an oral dose of greater than about 50 mg per day in a human. In a further aspect, the disclosed compounds promote muscle hypertrophy when administered at an oral dose of greater than about 75 mg per day in a human. In a further aspect, the disclosed compounds promote muscle hypertrophy when administered at an oral dose of greater than about 100 mg per day in a human. In a further aspect, the disclosed compounds promote muscle hypertrophy when administered at an oral dose of greater than about 150 mg per day in a human. In a further aspect, the disclosed promote muscle hypertrophy when administered at an oral dose of greater than about 200 mg per day in a human. In a further aspect, the disclosed compounds promote muscle hypertrophy when administered at an oral dose of greater than about 250 mg per day in a human. In a yet further aspect, the disclosed compounds promote muscle hypertrophy when administered at an oral dose of greater than about 300 mg per day in a human. In a still further aspect, the disclosed compounds promote muscle hypertrophy when administered at an oral dose of greater than about 400 mg per day in a human. In an even further aspect, the disclosed compounds promote muscle hypertrophy when administered at an oral dose of greater than about 500 mg per day in a human. In a further aspect, the disclosed compounds promote muscle hypertrophy when administered at an oral dose of greater than about 750 mg per day in a human. In a yet further aspect, the disclosed compounds promote muscle hypertrophy when administered at an oral dose of greater than about 1000 mg per day in a human. In a still further aspect, the disclosed compounds promote muscle hypertrophy when administered at an oral dose of greater than about 1500 mg per day in a human. In an even further aspect, the disclosed compounds promote muscle hypertrophy when administered at an oral dose of greater than about 2000 mg per day in a human.

5. Decrease of Adiposity

In one aspect, the disclosed compounds decrease adiposity. In a further aspect, the disclosed compounds reduce fat. For example, the disclosed compounds can reduce fat in an animal when administered in an effective amount. In a yet further aspect, the disclosed compounds increase the muscle to fat ratio. For example, the disclosed compounds increase the muscle mass and reduce the fat in an animal when administered in an effective amount. For example, the percentage muscle in an animal can increase while the percentage fat in the animal decreases. In a yet further aspect, the disclosed compounds can prevent an increase in fat. In a yet further aspect, the disclosed compounds decreases the fat content in an animal. In a yet further aspect, the disclosed compounds decrease obesity. In a yet further aspect, the disclosed compounds decrease complications of obesity such as type 2 diabetes, nonalcoholic fatty liver disease, obstructive sleep apnea and osteoarthritis. In a still further aspect, the animal is a mammal. In a yet further aspect, the mammal is a human. In a further aspect, the mammal is a mouse. In a yet further aspect, the mammal is a rodent. In a yet further aspect, the animal is a bird or a fish.

In a further aspect, the disclosed compounds decrease adiposity when administered at an oral dose of greater than about 5 mg per day in a human. In a further aspect, the disclosed compounds decrease adiposity when administered at an oral dose of greater than about 10 mg per day in a human. In a further aspect, the disclosed compounds decrease adiposity when administered at an oral dose of greater than about 25 mg per day in a human. In a further aspect, the disclosed compounds decrease adiposity when administered at an oral dose of greater than about 50 mg per day in a human. In a further aspect, the disclosed compounds decrease adiposity when administered at an oral dose of greater than about 75 mg per day in a human. In a further aspect, the disclosed compounds decrease adiposity when administered at an oral dose of greater than about 100 mg per day in a human. In a further aspect, the disclosed compounds decrease adiposity when administered at an oral dose of greater than about 150 mg per day in a human. In a further aspect, the disclosed compounds decrease adiposity when administered at an oral dose of greater than about 200 mg per day in a human. In a further aspect, the disclosed compounds decrease adiposity when administered at an oral dose of greater than about 250 mg per day in a human. In a yet further aspect, the disclosed compounds decrease adiposity when administered at an oral dose of greater than about 300 mg per day in a human. In a still further aspect, the disclosed compounds decrease adiposity when administered at an oral dose of greater than about 400 mg per day in a human. In an even further aspect, the disclosed compounds decrease adiposity when administered at an oral dose of greater than about 500 mg per day in a human. In a further aspect, the disclosed compounds decrease adiposity when administered at an oral dose of greater than about 750 mg per day in a human. In a yet further aspect, the disclosed compounds decrease adiposity when administered at an oral dose of greater than about 1000 mg per day in a human. In a still further aspect, the disclosed compounds decrease adiposity when administered at an oral dose of greater than about 1500 mg per day in a human. In an even further aspect, the disclosed compounds decrease adiposity when administered at an oral dose of greater than about 2000 mg per day in a human.

6. Inhibition of Muscle Atrophy

In one aspect, the disclosed compounds inhibit muscle atrophy. In a further aspect, the disclosed compounds promoting muscle health, promoting normal muscle function, and/or promoting healthy aging muscles. In a yet further aspect, the disclosed compounds inhibit of muscle atrophy and promote muscle health, promote normal muscle function, and/or promote healthy aging muscles. In a further aspect, the inhibition of muscle atrophy is in an animal. In an even further aspect, the promoting muscle health, promoting normal muscle function, and/or promoting healthy aging muscles is in an animal. In a still further aspect, the animal is a mammal. In a yet further aspect, the mammal is a human. In a further aspect, the mammal is a mouse. In a yet further aspect, the mammal is a rodent. In a yet further aspect, the animal is a bird or a fish.

In a further aspect, the disclosed compounds inhibit muscle atrophy when administered at an oral dose of greater than about 5 mg per day in a human. In a further aspect, the disclosed compounds inhibit muscle atrophy when administered at an oral dose of greater than about 10 mg per day in a human. In a further aspect, the disclosed compounds inhibit muscle atrophy when administered at an oral dose of greater than about 25 mg per day in a human. In a further aspect, the disclosed compounds inhibit muscle atrophy when administered at an oral dose of greater than about 50 mg per day in a human. In a further aspect, the disclosed compounds inhibit muscle atrophy when administered at an oral dose of greater than about 75 mg per day in a human. In a further aspect, the disclosed compounds inhibit muscle atrophy when administered at an oral dose of greater than about 100 mg per day in a human. In a further aspect, the disclosed compounds inhibit muscle atrophy when administered at an oral dose of greater than about 150 mg per day in a human. In a further aspect, the disclosed compounds inhibit muscle atrophy when administered at an oral dose of greater than about 200 mg per day in a human. In a further aspect, the disclosed compounds inhibit muscle atrophy when administered at an oral dose of greater than about 250 mg per day in a human. In a yet further aspect, the disclosed compounds inhibit muscle atrophy when administered at an oral dose of greater than about 300 mg per day in a human. In a still further aspect, the disclosed compounds inhibit muscle atrophy when administered at an oral dose of greater than about 400 mg per day in a human. In an even further aspect, the disclosed compounds inhibit muscle atrophy when administered at an oral dose of greater than about 500 mg per day in a human. In a further aspect, the disclosed compounds inhibit muscle atrophy when administered at an oral dose of greater than about 750 mg per day in a human. In a yet further aspect, the disclosed compounds inhibit muscle atrophy when administered at an oral dose of greater than about 1000 mg per day in a human. In a still further aspect, the disclosed compounds inhibit muscle atrophy when administered at an oral dose of greater than about 1500 mg per day in a human. In an even further aspect, the disclosed compounds inhibit muscle atrophy when administered at an oral dose of greater than about 2000 mg per day in a human.

It is contemplated that one or more compounds can optionally be omitted from the disclosed invention.

C. Pharmaceutical and Neutraceutical Compositions

In one aspect, the invention relates to pharmaceutical and neutraceutical compositions comprising the disclosed compounds. That is, a pharmaceutical composition can be provided comprising a therapeutically effective amount of at least one disclosed compound. In another example, a pharmaceutical composition can be provided comprising a prophylactically effective amount of at least one disclosed compound. In yet another example, a neutraceutical composition can be provided comprising a neutraceutically effective amount of at least one disclosed compound.

In one aspect, the invention relates to pharmaceutical compositions comprising a pharmaceutically acceptable carrier and a compound, wherein the compound is present in an effective amount. In another aspect, the invention relates to neutraceutical compositions comprising a neutraceutically acceptable carrier and a compound, wherein the compound is present in an effective amount. In one example, the compound can be a tomatidine analog.

In one aspect, the compound is present in an amount greater than about an amount selected from 5 mg, 10 mg, 25 mg, 50 mg, 100 mg, 150 mg, 200 mg, 250 mg, 300 mg, 400, mg, 500 mg, 750 mg, 1000 mg, 1,500 mg, or 2,000 mg.

A pharmaceutical composition comprising a pharmaceutically acceptable carrier and an effective amount of: (a) tomatidine or a tomatidine analog, (b) a compound that down regulates multiple induced mRNAs of Muscle Atrophy Signature 1, compared to expression levels in the same type of the muscle cell in the absence of the compound; (c) a compound that up regulates multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; (e) a compound that up regulates multiple mRNAs of Muscle Atrophy Signature 2, compared to expression levels in the same type of the muscle cell in the absence of the compound; (f) a compound that promotes muscle hyperplasia; and/or (g) a compound that increases the metabolism in an animal.

In a further aspect, the amount is a therapeutically effective amount. In a still further aspect, the amount is a prophylactically effective amount.

In a further aspect, pharmaceutical or neutraceutical composition is administered to an animal. In a still further aspect, the animal is a mammal, fish or bird. In a yet further aspect, the mammal is a primate. In a still further aspect, the mammal is a human. In an even further aspect, the human is a patient.

In a further aspect, the pharmaceutical composition comprises a compound identified using muscle atrophy signature-1. In a yet further aspect, the pharmaceutical composition comprises a compound identified using muscle atrophy signature-2. In a yet further aspect, the pharmaceutical composition comprises a compound identified using both muscle atrophy signature-1 and muscle atrophy signature-2.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, the muscle disorder is muscle atrophy. In an even further aspect, the muscle disorder is a condition in need of promoting muscle health, promoting normal muscle function, and/or promoting healthy aging muscles. In a yet further aspect, the muscle disorder is induced by another disease, such as cancer.

In a further aspect, the pharmaceutical composition is administered following identification of the mammal in need of treatment of muscle atrophy. In a still further aspect, the pharmaceutical composition is administered following identification of the mammal in need of prevention of muscle atrophy. In an even further aspect, the mammal has been diagnosed with a need for treatment of muscle atrophy prior to the administering step.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" and "neutraceutically acceptable salts" refers to salts prepared from pharmaceutically or neutraceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically or neutraceutically acceptable organic non-toxic bases from which salts can be formed include ion exchange resins such as, for example, arginine, betaine, caffeine, choline, N,N-dibenzylethyl enediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tris(hydroxymethyl) aminomethane, tromethamine and the like.

As used herein, the term "pharmaceutically acceptable non-toxic acids", includes inorganic acids, organic acids, and salts prepared thereof, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, or neutraceutically acceptable salts thereof, of this invention can be combined as the active ingredient in intimate admixture with a pharmaceutical carrier or neutraceutical carrier according to conventional pharmaceutical compounding techniques or conventional neutraceutical compounding techniques. The carrier can take a wide variety of forms depending on the form of preparation desired for administration, e.g., oral or parenteral (including intravenous). Thus, the pharmaceutical compositions or neutraceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

Thus, the neutraceutical compositions of this invention can include a neutraceutically acceptable carrier and a compound or a neutraceutically acceptable salt of the compounds of the invention. The compounds of the invention, or neutraceutically acceptable salts thereof, can also be included in neutraceutical compositions in combination with one or more other therapeutically or neutraceutically active compounds.

The pharmaceutical carrier or neutraceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions or neutraceutical compositions of the present invention comprise a compound of the invention (or pharmaceutically or neutraceutically acceptable salts thereof) as an active ingredient, a pharmaceutically acceptable carrier or neutraceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of cellular function related to muscle health, muscle function and/or healthy muscle aging an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

The compositions disclosed herein can be administered with one or more health supplements, such as energy or vitamin supplements. Suitable health supplements include, but are not limited to, protein bars, protein shakes, sports drinks, energy drinks, and multivitamins. The compositions can also be administered with other one or more compounds known to promote muscle hypertrophy, such as creatine.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating cellular activity related to muscle health, muscle function, and/or healthy aging muscles (e.g., treatment of one or more disorders associated with muscle dysfunction or atrophy) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

D. Methods of Using the Compounds and Compositions

1. Muscle Hypertrophy

Muscle hypertrophy is defined as the increase in muscle size or mass of the muscle, and can include an increase in individual fiber volume and/or an increase in the cross-sectional area of myofibers, and may also include an increase in the number of nuclei per muscle fiber. Muscle hypertrophy can also include an increase in the volume and mass of whole muscles; however, muscle hypertrophy can be differentiated from muscle hyperplasia, which is an increased number of muscle fibers. In one embodiment, muscular hypertrophy refers to an increase in the number of actin and myosin contractile proteins. Muscle hypertrophy leads to an increase in muscle strength. The muscle can be skeletal muscle.

The disclosed compounds can be used as single agents or in combination with one or more other drugs to promote muscle hypertrophy, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

Systemic administration of one or more disclosed compounds (e.g., by parenteral injection or by oral consumption) can be used to increase muscle mass, increase muscle hypertrophy, increase cellular protein, and promote growth of muscle cells. Local administration of a disclosed compound (by a topical route or localized injection) can be used to promote muscle hypertrophy, as can be required following a localized injury or surgery.

In one aspect, the subject compounds can be coadministered with agents that increase skeletal muscle mass, increase skeletal muscle strength, increase exercise capacity, increase skeletal muscle anabolic signaling, increase skeletal muscle protein synthesis, increase skeletal muscle mitochondria and/or increase skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog, Wnt7a, an activator of Wnt7a signaling, an activator of TRPV1, an activator of $G\alpha i_2$ signaling, an activator of PGC-1α4 signaling, or branched chain amino acids. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

In another aspect, the subject compounds can be administered in combination with agents that increase skeletal muscle mass, skeletal muscle strength, increase exercise capacity, increase skeletal muscle anabolic signaling, increase skeletal muscle protein synthesis, increase skeletal muscle mitochondria and/or skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog, Wnt7a, an activator of Wnt7a signaling, an activator of TRPV1, an activator of $G\alpha i_2$ signaling, an activator of PGC-1α4 signaling, or branched chain amino acids. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

2. Adiposity

Adiposity is defined as the fat fraction of the body of an animal. Decreasing adiposity refers to a decrease of the fat fraction of the body of an animal. This can be achieved by either lowering the amount of fat of the body of an animal or by increasing the fat-free mass of the body of the animal, such as increasing the mass of muscle of the body in the animal. In one aspect, adiposity can refer to lowering the amount of fat of the body of an animal.

In one aspect, the animal can have high body adiposity. High body adiposity refers to a fat fraction above 30%, 35% or 40%. The adiposity, such as high body adiposity, can be the effect of an underlying disease or a side effect of a drug. Such disease and drugs are known in the art. For example, administration of corticosteroids (such as deltasone or prednisone) and/or antidepressants (such as Prozac and Zoloft) and/or antipsychotics (including but not limited to clozapine, olanzapine, risperidone and quetiapine) can increase the adiposity in an animal. Also, diseases that severely decrease mobility and an animal's ability to exercise can cause high body adiposity.

The disclosed compounds can be used as single agents or in combination with one or more other drugs to decrease adiposity, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

Systemic administration of one or more disclosed compounds (e.g., by parenteral injection or by oral consumption) can be used to reduce fat, increase the muscle to fat ratio, increase the muscle mass and reduce the fat, and prevent an increase in fat in an animal. Local administration of a disclosed compound (by a topical route or localized injection) can be used to decrease adiposity.

In one aspect, the subject compounds can be coadministered with agents that decrease adiposity, increase the ratio of skeletal muscle to adipose tissue, increase energy expenditure, decrease appetite, increase skeletal muscle mass, increase skeletal muscle strength, increase exercise capacity, increase skeletal muscle anabolic signaling, increase skeletal muscle protein synthesis, increase skeletal muscle mitochondria and/or increase skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog, Wnt7a, an activator of Wnt7a signaling, an activator of TRPV1, an activator of Gαi$_2$ signaling, an activator of PGC-1α4 signaling, or branched chain amino acids. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

In another aspect, the subject compounds can be administered in combination with decrease adiposity, increase the ratio of skeletal muscle to adipose tissue, increase energy expenditure, decrease appetite, increase skeletal muscle mass, increase skeletal muscle strength, increase exercise capacity, increase skeletal muscle anabolic signaling, increase skeletal muscle protein synthesis, increase skeletal muscle mitochondria and/or increase skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog, Wnt7a, an activator of Wnt7a signaling, an activator of TRPV1, an activator of Gαi$_2$ signaling, an activator of PGC-1α4 signaling, or branched chain amino acids. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

3. Muscle Atrophy

Muscle atrophy is defined as a decrease in the mass of the muscle; it can be a partial or complete wasting away of muscle. When a muscle atrophies, this leads to muscle weakness, since the ability to exert force is related to mass. Muscle atrophy is a co-morbidity of several common diseases, and patients who have "cachexia" in these disease settings have a poor prognosis.

Muscle atrophy can also be skeletal muscle loss or weakness caused by malnutrition, aging, bed rest, neurologic disease (such as multiple sclerosis, amyotrophic lateral sclerosis, spinal muscular atrophy, critical illness neuropathy, spinal cord injury, peripheral neuropathy, or peripheral nerve injury), injury to the limbs or joints, casting, other post-surgical forms of limb immobilization, or spaceflight, chronic disease (such as cancer, congestive heart failure, chronic pulmonary disease, chronic renal failure, chronic liver disease, diabetes mellitus, glucocorticoid excess, growth hormone deficiency, IGF-I deficiency, estrogen deficiency, and chronic infections such as HIV/AIDS or tuberculosis), burn injuries, sepsis, other illnesses requiring mechanical ventilation, drug-induced muscle disease (such as glucocorticoid-induced myopathy and statin-induced myopathy), genetic diseases that primarily affect skeletal muscle (such as muscular dystrophy, myotonic dystrophy and inclusion body myositis), or autoimmune diseases that affect skeletal muscle (such as polymyositis and dermatomyositis).

There are many diseases and conditions which cause muscle atrophy, including malnutrition, bed rest, neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome, growth hormone deficiency, IGF-I deficiency, estrogen deficiency, and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, and aging.

Muscle atrophy occurs by a change in the normal balance between protein synthesis and protein degradation. During atrophy, there is a down-regulation of protein synthesis pathways, and an activation of protein breakdown pathways. The particular protein degradation pathway which seems to be responsible for much of the muscle loss seen in a muscle undergoing atrophy is the ATP-dependent, ubiquitin/proteasome pathway. In this system, particular proteins are targeted for destruction by the ligation of at least four copies of a small peptide called ubiquitin onto a substrate protein. When a substrate is thus "poly-ubiquitinated," it is targeted for destruction by the proteasome. Particular enzymes in the ubiquitin/proteasome pathway allow ubiquitination to be directed to some proteins but not others—specificity is gained by coupling targeted proteins to an "E3 ubiquitin ligase." Each E3 ubiquitin ligase binds to a particular set of substrates, causing their ubiquitination. For example, in skeletal muscle, the E3 ubiquitin ligases atrogin-1 and MuRF1 are known to play essential roles protein degradation and muscle atrophy.

Muscle atrophy can be opposed by the signaling pathways which induce muscle hypertrophy, or an increase in muscle size. Therefore one way in which exercise induces and promote muscle health, promote normal muscle function, and/or promote healthy aging muscles is to down regulate the pathways which have the opposite effects. One important rehabilitation tool for muscle atrophy includes the use of functional electrical stimulation to stimulate the muscles which has had limited success in the rehabilitation of paraplegic patients.

In certain aspects, the disclosed compounds can be used as a therapy for illness- and age-related muscle atrophy. It can be useful as a monotherapy or in combination with other strategies that have been considered, such as myostatin inhibition (Zhou, X., et al. (2010) Cell 142(4): 531-543). Given its capacity to reduce adiposity, fasting blood glucose and plasma lipid levels, a disclosed compound derivative can also be used as a therapy for obesity, metabolic syndrome and type 2 diabetes.

The disclosed compounds can be used as single agents or in combination with one or more other drugs in the treatment, prevention, control, amelioration or reduction of risk of the aforementioned diseases, disorders and conditions for which the compounds disclosed herein or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

Systemic administration of one or more disclosed compounds (e.g., by parenteral injection or by oral consumption) can be used to promote muscle health, promote normal muscle function, and/or promote healthy aging muscles, and reduce muscle atrophy in all muscles, including those of the limbs and the diaphragm. Local administration of a disclosed compound (by a topical route or localized injection) can be used to promote local muscle health, as can be required following a localized injury or surgery.

In one aspect, the subject compounds can be coadministered with agents that decrease muscle atrophy, increase skeletal muscle mass, skeletal muscle strength, skeletal muscle insulin signaling, skeletal muscle IGF-I signaling and/or skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

In another aspect, the subject compounds can be administered in combination with agents that decrease muscle atrophy, increase skeletal muscle mass, skeletal muscle strength, skeletal muscle insulin signaling, skeletal muscle IGF-I signaling and/or skeletal muscle glucose uptake including but not limited to ursolic acid, ursolic acid analogs, betulinic acid, betulinic acid analogs, tacrine, tacrine analogs, allantoin, allantoin analogs, connesine, connesine analogs, naringenin, naringenin analogs, hippeastrine, hippeastrine analogs, ungerine, ungerine analogs, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, TGF-beta signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

The pharmaceutical compositions and methods of the present invention can further comprise other therapeutically active compounds as noted herein which are usually applied in the treatment of the above mentioned pathological conditions.

4. Treatment Methods

The compounds disclosed herein are useful for promoting or increasing muscle hypertrophy. The compounds are also useful for increasing muscle mass, increasing muscle hypertrophy, increasing muscle strength, increasing cellular protein, and promoting growth of muscle cells.

The compounds disclosed herein are also useful to decrease adiposity. The compounds are also useful for reducing fat, increasing the muscle to fat ratio, increasing the muscle mass and reducing the fat, preventing an increase in fat in an animal, decreasing obesity, and decreasing complications of obesity. The adiposity, such as high body adiposity, can be the effect of an underlying disease or a side effect of a drug. For example, administration of corticosteroids (such as deltasone or prednisone) and/or antidepressants (such as Prozac and Zoloft) and/or antipsychotics (including but not limited to clozapine, olanzapine, risperidone and quetiapine) can increase the adiposity in an animal. Also, diseases that severely decrease mobility and an animal's ability to exercise can cause high body adiposity.

The compounds disclosed herein are useful for treating, preventing, ameliorating, controlling or reducing the risk of a variety of muscle disorders. Examples of such muscle disorders include, but are not limited to, skeletal muscle atrophy secondary to malnutrition, bed rest, neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia. In still further aspects, the invention is related to methods to modulate muscle health, methods to inhibit muscle atrophy.

Thus, provided is a method for treating or preventing muscle atrophy, comprising: administering to a subject at least one disclosed compound; at least one disclosed pharmaceutical composition; and/or at least one disclosed product in a dosage and amount effective to treat the disorder in the subject.

Also provided is a method for promoting muscle health, promote normal muscle function, and/or promote healthy aging muscles comprising: administering to a subject at least one disclosed compound; at least one disclosed pharmaceutical composition; and/or at least one disclosed product in a dosage and amount effective to treat the disorder in the subject.

The compounds disclosed herein are useful for treating, preventing, ameliorating, controlling or reducing the risk of a variety of metabolic disorders. In a further aspect, the disclosed compounds in treating disorders associated with a dysfunction of insulin/IGF-I signaling. Thus, are provided methods to increase insulin/IGF-I signaling, methods to reduce body fat; methods to reduce blood glucose, methods to reduce blood triglycerides, methods to reduce blood cholesterol, methods to reduce obesity, methods to reduce fatty liver disease, and methods to reduce diabetes, and pharmaceutical compositions comprising compounds used in the methods.

a. Promoting Muscle Hypertrophy

Disclosed herein is a method of promoting muscle hypertrophy in an animal comprising administering to the animal an effective amount of a compound disclosed herein. The compound can be tomatidine, or tomatidine analogs, or a mixture thereof. For example, the compound can be a tomatidine analog. In another example, the compound can be tomatidine. In yet another example, the compound can be a mixture of tomatidine and tomatidine analogs.

In one aspect, the compound is administered in an amount between about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

In one aspect, the disclosed compounds increase muscle hypertrophy. In another aspect, the disclosed compounds increase muscle mass. In a further aspect, the disclosed compounds increase cellular protein. In a still further aspect, the disclosed compounds promote protein synthesis. In yet a further aspect, the disclosed compounds increase mitochondria.

In yet another aspect, the disclosed compounds promote growth of muscle cells.

In a further aspect, the compound administered is a disclosed compound or a product of a disclosed method of making a compound. In a yet further aspect, the invention relates to a pharmaceutical composition comprising at least one compound as disclosed herein.

In a further aspect, the compound is co-administered with an anabolic agent. In a further aspect, wherein the compound is co-administered with ursolic acid or an ursolic acid derivative. In a further aspect, the compound is co-administered with a compound selected from a tacrine and analogs, naringenin and analogs, allantoin and analogs, conessine and analogs, ungerine/hippeastrine and analogs, and betulinic acid and analogs, or a mixture thereof.

In a further aspect, the animal is a mammal, fish or bird. In a yet further aspect, the mammal is a primate. In a still further aspect, the mammal is a human. In an even further aspect, the human is a patient.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a still further aspect, the method further comprises the step of identifying the mammal in need of muscle hypertrophy. In an even further aspect, the mammal has been diagnosed with a need for muscle hypertrophy which can be treated by muscle hypertrophy prior to the administering step.

b. Decreasing Adiposity

Disclosed herein is a method of decreasing adiposity in an animal comprising administering to the animal an effective amount of a compound disclosed herein. The compound can be tomatidine, or tomatidine analogs, or a mixture thereof. For example, the compound can be a tomatidine analog. In another example, the compound can be tomatidine. In yet another example, the compound can be a mixture of tomatidine and tomatidine analogs.

In one aspect, the compound is administered in an amount between about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

In one aspect, the disclosed compounds decrease adiposity. In another aspect, the disclosed compounds reduce fat, such as the amount of fat of an animal. In another aspect, the disclosed compounds increase the muscle to fat ratio. In another aspect, the disclosed compounds increase the muscle mass and reduce the fat. In another aspect, the disclosed compounds prevent an increase in fat.

In a further aspect, the compound administered is a disclosed compound or a product of a disclosed method of making a compound. In a yet further aspect, the invention relates to a pharmaceutical composition comprising at least one compound as disclosed herein.

In a further aspect, the compound is co-administered with an anabolic agent. In a further aspect, wherein the compound is co-administered with ursolic acid or a ursolic acid derivative. In a further aspect, the compound is co-administered with a compound selected from a tacrine and analogs, naringenin and analogs, allantoin and analogs, conessine and analogs, ungerine/hippeastrine and analogs, and betulinic acid and analogs, or a mixture thereof.

In a further aspect, the animal is a mammal, fish or bird. In a yet further aspect, the mammal is a primate. In a still further aspect, the mammal is a human. In an even further aspect, the human is a patient.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, high adiposity is prevented by administration of the compound. In an even further aspect, adiposity is decreased by administration of the compound. In a still further aspect, the method further comprises the step of identifying the mammal in need of decreased adiposity. In a yet further aspect, the method further comprises the step of identifying the mammal in a need of prevention of adiposity. In an even further aspect, the mammal has been diagnosed with a need for treatment of adiposity prior to the administering step.

c. Treating Muscle Atrophy

Disclosed herein is a method of treating muscle atrophy in an animal comprising administering to the animal an effective amount of a compound. The compound can be tomatidine, or tomatidine analogs, or a mixture thereof. For example, the compound can be a tomatidine analog. In another example, the compound can be tomatidine. In yet another example, the compound can be a mixture of tomatidine and tomatidine analogs.

In one aspect, the compound is administered in an amount between about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

In one aspect, the disclosed compounds inhibit muscle atrophy. In a further aspect, the disclosed compounds promote muscle health, promote normal muscle function, and/or promote healthy aging muscles. In a yet further aspect, the disclosed compounds inhibit of muscle atrophy and promoting muscle health, promoting normal muscle function, and/or promoting healthy aging muscles. In an even further aspect, the disclosed compounds treat muscle atrophy.

In a further aspect, the compound administered is a disclosed compound or a product of a disclosed method of making a compound. In a yet further aspect, the invention relates to a pharmaceutical composition comprising at least one compound as disclosed herein.

In a further aspect, the compound is co-administered with an anabolic agent. In a further aspect, wherein the compound is co-administered with ursolic acid or an ursolic acid derivative.

In a further aspect, the animal is a mammal, fish or bird. In a yet further aspect, the mammal is a primate. In a still further aspect, the mammal is a human. In an even further aspect, the human is a patient.

In a further aspect, prior to the administering step the mammal has been diagnosed with a need for treatment of a disorder selected muscle atrophy, diabetes, obesity, and fatty liver disease. In a yet further aspect, the disorder is muscle atrophy.

In a further aspect, prior to the administering step the mammal has been diagnosed with a need for treatment of a disorder associated with a dysfunction in anabolic signaling.

In a further aspect, the treatment of the disorder increases muscle anabolic signaling. In a still further aspect, the treatment of the disorder increases muscle IGF-I production.

In a further aspect, prior to the administering step the mammal has been diagnosed with a need for treatment of a disorder associated with circulating levels of leptin. In a still further aspect, the treatment decreases the circulating levels of leptin.

In a further aspect, administration the methods are promoting muscle health, promoting normal muscle function, and/or promoting healthy aging muscles in the mammal. In a yet further aspect, administration increases energy expenditure. In a still further aspect, increases brown fat. In an even further aspect, administration increases the ratio of brown fat to white fat. In a still further aspect, administration increases the ratio of skeletal muscle to fat. In a yet further aspect, the compound is co-administered with a disclosed compound or a derivative thereof.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in a need of prevention of muscle atrophy. In an even further aspect, the mammal has been diagnosed with a need for treatment of muscle atrophy prior to the administering step.

d. Promoting Muscle Health

In one aspect, the invention relates to a method for promoting muscle health, promoting normal muscle function, and/or promoting healthy aging muscles in an animal, the method comprising administering to the animal an effective amount of tomatidine. In one aspect, the invention relates to a method for promoting muscle health. In another aspect, the invention relates to a method for promoting normal muscle function. In another aspect, the invention relates to a method for promoting healthy aging muscles.

In one aspect, the invention relates to a method for promoting muscle health, promoting normal muscle function, and/or promoting healthy aging muscles in an animal, the method comprising administering to the animal an effective amount of a compound, wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles in the animal.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, prior to the administering step the mammal has been diagnosed with a need for treatment of a disorder selected muscle atrophy, diabetes, obesity, and fatty liver disease. In a yet further aspect, the disorder is muscle atrophy.

In a further aspect, prior to the administering step the mammal has been diagnosed with a need for treatment of a disorder associated with a dysfunction in anabolic signaling.

In a further aspect, the treatment of the disorder increases muscle anabolic signaling. In a still further aspect, the treatment of the disorder increases muscle IGF-I production.

In a further aspect, prior to the administering step the mammal has been diagnosed with a need for treatment of a disorder associated with circulating levels of leptin. In a still further aspect, the treatment decreases the circulating levels of leptin.

In a further aspect, administration promoting muscle health, promoting normal muscle function, and/or promoting healthy aging muscles in the mammal. In a yet further aspect, administration increases energy expenditure. In a still further aspect, increases brown fat. In an even further aspect, administration increases the ratio of brown fat to white fat. In a still further aspect, administration increases the ratio of skeletal muscle to fat. In a yet further aspect, the compound is co-administered with a disclosed compound or a derivative thereof.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in a need of prevention of muscle atrophy. In an even further aspect, the mammal has been diagnosed with a need for treatment of muscle atrophy prior to the administering step.

e. Enhancing Muscle Formation

In one aspect, the invention relates to a method of enhancing muscle formation in a mammal, the method comprising administering to the animal an effective amount of tomatidine.

In a further aspect, the invention relates to a method of enhancing muscle formation in a mammal, the method comprising administering to the animal an effective amount of a compound, wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles in the animal.

In a further aspect, the mammal is a human. In a still further aspect, the human is a patient. In a yet further aspect, administration of the compound prevents muscle atrophy in the mammal. In an even further aspect, administration of the compound treats muscle atrophy in the mammal. In a still further aspect, administration of the compound promotes muscle health, promote normal muscle function, and/or promote healthy aging muscles in the mammal.

In a further aspect, the compound is administered in an effective amount. In a yet further aspect, the effective amount is a therapeutically effective amount. In a still further aspect, the effective amount is a prophylactically effective amount. In a still further aspect, the method further comprises the step of identifying the mammal in need of treatment of muscle atrophy. In a yet further aspect, the method further comprises the step of identifying the mammal in need of prevention of muscle atrophy. In an even further aspect, the mammal has been diagnosed with a need for treatment of muscle atrophy prior to the administering step.

In a further aspect, the mammal is a domesticated animal. In a yet further aspect, domesticated animal is livestock. In a yet further aspect, the livestock animal is selected from pig, cow, horse, goat, bison, and sheep.

f. Increasing Exercise Capacity

In one aspect, the invention relates to a method of increasing exercise capacity in a mammal, the method comprising administering to the animal an effective amount of tomatidine.

In a further aspect, the invention relates to a method of increasing exercise capacity in a mammal, the method comprising administering to the animal an effective amount of a compound, wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles in the animal.

In a further aspect, the mammal is a human. In a still further aspect, the human is a patient. In a yet further aspect, administration of the compound prevents muscle atrophy in the mammal. In an even further aspect, administration of the compound treats muscle atrophy in the mammal. In a still further aspect, administration of the compound promotes muscle health, promote normal muscle function, and/or promote healthy aging muscles in the mammal.

In a further aspect, the compound is administered in an effective amount. In a yet further aspect, the effective amount is a therapeutically effective amount. In a still further aspect, the effective amount is a prophylactically effective amount. In a still further aspect, the method further comprises the step of identifying the mammal in need of treatment of muscle atrophy. In a yet further aspect, the method further comprises the step of identifying the mammal in need of prevention of muscle atrophy. In an even further aspect, the mammal has been diagnosed with a need for treatment of muscle atrophy prior to the administering step.

In a further aspect, the mammal is a domesticated animal. In a yet further aspect, domesticated animal is livestock. In a yet further aspect, the livestock animal is selected from pig, cow, horse, goat, bison, and sheep.

5. Facilitating Tissue Formation In Vitro

In one aspect, the invention relates to a method of enhancing tissue health in vitro, the method comprising administering to the tissue an effective amount of a compound wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles.

In a further aspect, the compound administered is a disclosed compound. In a further aspect, the compound is tomatidine.

In a further aspect, the tissue comprises animal cells. In a still further aspect, the animal cells are muscle cells. In a yet further aspect, the muscle cells are skeletal muscle stem or progenitor cells. In an even further aspect, the skeletal muscle stem or progenitor cells are grown on a scaffold.

6. Manufacture of a Medicament

In one aspect, the invention relates to a method for the manufacture of a medicament for inhibiting muscle atrophy and for promoting muscle health, promoting normal muscle function, and/or promoting healthy aging muscles in a mammal comprising combining a therapeutically effective amount of a disclosed compound or product of a disclosed method with a pharmaceutically acceptable carrier or diluent.

In one aspect, the invention relates to a method for manufacturing a medicament associated with muscle atrophy or the need to promote muscle health, promote normal muscle function, and/or promote healthy aging muscles, the method comprising the step of combining an effective amount of one or more of: (a) tomatidine, tomatidine analog, or a mixture thereof; (b) a compound that down regulates multiple induced mRNAs of Muscle Atrophy Signature 1, compared to expression levels in the same type of the muscle cell in the absence of the compound; (c) a compound that up multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; and/or (e) a compound that up regulates at least one of the repressed mRNAs of Muscle Atrophy Signature 2, compared to expression levels in the same type of the muscle cell in the absence of the compound, with a pharmaceutically acceptable carrier or diluent.

In a further aspect, the medicament comprises a disclosed compound. In a still further aspect, the compound is tomatidine.

In a further aspect, the medicament modulates muscle health. In a still further aspect, the medicament inhibits muscle atrophy. In a yet further aspect, the medicament promote muscle health, promote normal muscle function, and/or promote healthy aging muscles.

7. Kits

Also disclosed herein are kit comprising tomatidine or a tomatidine analog, and one or more of: a) at least one agent known to promote muscle hypertrophy in an animal; b) at least one agent known to decrease adiposity in an animal; c) at least one agent known to have a side effect of promoting adiposity; d) at least one agent known to promote skeletal muscle atrophy; e) instructions for promoting muscle hypertrophy; f) instructions for decreasing adiposity; g) or at least one anabolic agent.

In one aspect, the kit further comprises at least one agent, wherein the compound and the agent are co-formulated.

In another aspect, the compound and the agent are co-packaged. The agent can be any agent as disclosed herein, such as anabolic agent, agent known to have a side effect of muscle atrophy, agent known to decrease the risk of obtaining muscle atrophy in an animal, or agent known to treat muscle atrophy in an animal.

In one aspect, the invention relates to a kit comprising an effective amount of one or more of: (a) a tomatidine analog; (b) a compound that down regulates multiple induced mRNAs of Muscle Atrophy Signature 1, compared to expression levels in the same type of the muscle cell in the absence of the compound; (c) a compound that up regulates multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; and/or (e) a compound that up regulates multiple repressed mRNAs of Muscle Atrophy Signature 2, compared to expression levels in the same type of the muscle cell in the absence of the compound, (f) and one or more of: (i) a protein supplement; (ii) an anabolic agent; (iii) a catabolic agent; (iv) a dietary supplement; (v) at least one agent known to treat a disorder associated with muscle wasting; (vi) instructions for treating a disorder associated with cholinergic activity; or (vii) instructions for using the compound to promote muscle health, promote normal muscle function, and/or promote healthy aging muscles.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

8. Identification of Compounds that Inhibit Muscle Atrophy

Also disclosed are methods for identifying a compound that inhibits muscle atrophy when administered in an effective amount to an animal in need of treatment thereof, the method comprising the steps of: (i) selecting a candidate compound; (ii) determining the effect of the candidate compound on a cell's expression levels of a plurality of induced mRNAs and/or repressed mRNAs of a Muscle Atrophy Signature, wherein the candidate compound is identified as suitable for muscle atrophy inhibition if: (a) more than one of the induced mRNAs of the Muscle Atrophy Signature are down regulated, compared to expression levels of the induced mRNAs of the Muscle Atrophy Signature in the same type of cell in the absence of the candidate compound; and/or (b) more than one of the repressed mRNAs of the Muscle Atrophy Signature are up regulated, compared to expression levels of the repressed mRNAs of the Muscle Atrophy Signature in the same type of cell in the absence of the candidate compound. In one aspect, the method further comprises administering the candidate compound to an animal. In yet another aspect, the method further comprises writing a report. In yet another aspect, the method further comprises reporting the results. In yet another aspect, the method further comprises performing further tests on the candidate compound, such as confirmatory tests. In yet another aspect, the method further comprises performing toxicity studies on the candidate compound.

In a further aspect, the candidate compound comprises a disclosed compound. In a still further aspect, the compound is tomatidine.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, the Muscle Atrophy Signature is determined according to steps comprising: a) determining mRNA expression levels in a muscle cell undergoing muscle atrophy, b) determining mRNA expression levels in a muscle cell not undergoing muscle atrophy, wherein an mRNA is determined to be part of the Muscle Atrophy Signature if: (a) the mRNA is up regulated in the muscle cell undergoing muscle atrophy compared to the muscle cell not undergoing muscle atrophy, or (b) the mRNA is down regulated in the muscle cell undergoing muscle atrophy compared to the muscle cell not undergoing muscle atrophy.

In one aspect, the muscle cell undergoing atrophy and the muscle cell not undergoing atrophy are harvested from an animal. In another aspect, the muscle cell undergoing atrophy is harvested while the animal is in a state of fasting and the muscle cell not undergoing atrophy is harvested prior to the state of fasting. In yet another aspect, the muscle cell undergoing atrophy is harvested from an immobilized muscle and the muscle cell not undergoing atrophy is harvested from a mobile muscle. In yet another aspect, the muscle cell undergoing atrophy is harvested from an animal with spinal cord injury and the muscle cell not undergoing atrophy is harvested from a muscle that has received electrical stimulation. In yet another aspect, the Muscle Atrophy Signature is determined by selecting mRNAs commonly up regulated or commonly down regulated between two or more of the Muscle Atrophy Signatures of the methods described herein.

In a further aspect, the invention relates to a method for inhibiting muscle atrophy in a mammal, the method comprising administering to the mammal a therapeutically effective amount of a compound of identified using the method described above.

9. Identification of Compounds that Stimulate Muscle Hypertrophy

Also disclosed are methods for identifying a compound that stimulate muscle hypertrophy when administered in an effective amount to an animal in need of treatment thereof, the method comprising the steps of: (i) selecting a candidate compound; (ii) determining the effect of the candidate compound on a cell's expression levels of a plurality of induced mRNAs and/or repressed mRNAs of a Muscle Atrophy Signature, wherein the candidate compound is identified as suitable for stimulating muscle hypertrophy if: (a) more than one of the induced mRNAs of the Muscle Atrophy Signature are down regulated, compared to expression levels of the induced mRNAs of the Muscle Atrophy Signature in the same type of cell in the absence of the candidate compound; and/or (b) more than one of the repressed mRNAs of the Muscle Atrophy Signature are up regulated, compared to expression levels of the repressed mRNAs of the Muscle Atrophy Signature in the same type of cell in the absence of the candidate compound. In one aspect, the method further comprises administering the candidate compound to an animal. In yet another aspect, the method further comprises writing a report. In yet another aspect, the method further comprises reporting the results. In yet another aspect, the method further comprises performing further tests on the candidate compound, such as confirmatory tests. In yet another aspect, the method further comprises performing toxicity studies on the candidate compound.

In a further aspect, the candidate compound comprises a disclosed compound. In a still further aspect, the compound is tomatidine.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, the Muscle Atrophy Signature is determined according to steps comprising: a) determining mRNA expression levels in a muscle cell undergoing muscle atrophy, b) determining mRNA expression levels in a muscle cell not undergoing muscle atrophy, wherein an mRNA is determined to be part of the Muscle Atrophy Signature if: (a) the mRNA is up regulated in the muscle cell undergoing muscle atrophy compared to the muscle cell not undergoing muscle atrophy, or (b) the mRNA is down regulated in the muscle cell undergoing muscle atrophy compared to the muscle cell not undergoing muscle atrophy.

In one aspect, the muscle cell undergoing atrophy and the muscle cell not undergoing atrophy are harvested from an animal. In another aspect, the muscle cell undergoing atrophy is harvested while the animal is in a state of fasting and the muscle cell not undergoing atrophy is harvested prior to the state of fasting. In yet another aspect, the muscle cell undergoing atrophy is harvested from an immobilized muscle and the muscle cell not undergoing atrophy is harvested from a mobile muscle. In yet another aspect, the muscle cell undergoing atrophy is harvested from an animal with spinal cord injury and the muscle cell not undergoing atrophy is harvested from a muscle that has received electrical stimulation. In yet another aspect, the Muscle Atrophy Signature is determined by selecting mRNAs commonly up regulated or commonly down regulated between two or more of the Muscle Atrophy Signatures of the methods described herein.

In a further aspect, the invention relates to a method for stimulating muscle hypertrophy in a mammal, the method comprising administering to the mammal a therapeutically effective amount of a compound of identified using the method described above.

10. Identification of Compounds that Decrease Adiposity

Also disclosed are methods for identifying a compound that decrease adiposity when administered in an effective amount to an animal in need of treatment thereof, the method comprising the steps of: (i) selecting a candidate compound; (ii) determining the effect of the candidate compound on a cell's expression levels of a plurality of induced mRNAs and/or repressed mRNAs of a Muscle Atrophy Signature, wherein the candidate compound is identified as suitable for decreasing adiposity if: (a) more than one of the induced mRNAs of the Muscle Atrophy Signature are down regulated, compared to expression levels of the induced mRNAs of the Muscle Atrophy Signature in the same type of cell in the absence of the candidate compound; and/or (b) more than one of the repressed mRNAs of the Muscle Atrophy Signature are up regulated, compared to expression levels of the repressed mRNAs of the Muscle Atrophy Signature in the same type of cell in the absence of the candidate compound. In one aspect, the method further comprises administering the candidate compound to an animal. In yet another aspect, the method further comprises writing a report. In yet another aspect, the method further comprises reporting the results. In yet another aspect, the method further comprises performing further tests on the candidate compound, such as confirmatory tests. In yet another aspect, the method further comprises performing toxicity studies on the candidate compound.

In a further aspect, the candidate compound comprises a disclosed compound. In a still further aspect, the compound is tomatidine.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, the Muscle Atrophy Signature is determined according to steps comprising: a) determining mRNA expression levels in a muscle cell undergoing muscle atrophy, b) determining mRNA expression levels in a muscle cell not undergoing muscle atrophy, wherein an mRNA is determined to be part of the Muscle Atrophy Signature if: (a) the mRNA is up regulated in the muscle cell undergoing muscle atrophy compared to the muscle cell not undergoing muscle atrophy, or (b) the mRNA is down regulated in the muscle cell undergoing muscle atrophy compared to the muscle cell not undergoing muscle atrophy.

In one aspect, the muscle cell undergoing atrophy and the muscle cell not undergoing atrophy are harvested from an animal. In another aspect, the muscle cell undergoing atrophy is harvested while the animal is in a state of fasting and the muscle cell not undergoing atrophy is harvested prior to the state of fasting. In yet another aspect, the muscle cell undergoing atrophy is harvested from an immobilized muscle and the muscle cell not undergoing atrophy is harvested from a mobile muscle. In yet another aspect, the muscle cell undergoing atrophy is harvested from an animal with spinal cord injury and the muscle cell not undergoing atrophy is harvested from a muscle that has received electrical stimulation. In yet another aspect, the Muscle Atrophy Signature is determined by selecting mRNAs commonly up regulated or commonly down regulated between two or more of the Muscle Atrophy Signatures of the methods described herein.

In a further aspect, the invention relates to a method for decreasing adiposity in a mammal, the method comprising administering to the mammal a therapeutically effective amount of a compound of identified using the method described above.

11. Non-Medical Uses

Also provided are the uses of the disclosed compounds and products as pharmacological tools in the development and standardization of in vitro and in vivo test systems for the evaluation of the effects of inhibitors of muscle atrophy related activity in laboratory animals such as cats, dogs, rabbits, monkeys, rats, fish, birds, and mice, as part of the search for new therapeutic agents of promoting muscle health, promoting normal muscle function, and/or promoting healthy aging muscles.

Also provided are methods increasing muscle mass in domesticated animals, such as animals suitable for meat production, comprising administering to the domesticated animal an effective amount of the disclosed compounds. In one aspect, the disclosed compound is tomatidine. Animals suitable for meat production include, but are not limited to cows, bulls, bison, horses, sheep, goats, pigs, ducks, geese, lamas, camels, dromedary, boars, turkeys, and chickens.

E. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Certain materials, reagents and kits were obtained from specific vendors as indicated below, and as appropriate the vendor catalog, part or other number specifying the item are indicated. Vendors indicated below are as follows: "Ambion" is Ambion, a division of Life Technologies Corporation, Austin, Tex., USA; "Applied Biosystems" is Applied Biosystems, a division of Life Technologies Corporation, Carlsbad, Calif., USA; "Boehringer Mannheim" is Boehringer Mannheim Corporatin, Indiapolis, Ind., USA; "CardinalHealth" is Cardinal Health, Inc., Dublin, Ohio, USA; "Cell Signaling" is Cell Signaling Technology, Inc., Beverly, Massachussetts, USA; "Columbus Inst" is Columbus Instruments International, Columbus, Ohio, USA; "Harlan" is Harlan Laboratories, Indianapolis, Ind., USA; "Instrumedics" is Instrumedics, Inc., Richmond, Ill., USA; "Invitrogen" is Invitrogen Corporation, Carlsbad, Calif., USA; "Microm" is the Microm division (Walldorf, Germany) of Thermo Fisher Scientific Inc., Rockford, Ill., USA; "Millipore" is Millipore Corporation, Billerica, Massachussetts, USA; a division of Merck KGaA, Darmstadt, Germany; "Ortho" is Ortho Clinical Diagnostics, Rochester, N.Y., USA; "Pierce" is Pierce Biotechnology, Inc., Milwaukee, Wis., USA, a division of Thermo Fisher Scientific, Inc.; "R&D Systems" is R&D Systems Inc., Minneapolis, Minn., USA; "Roche Diagnostics" is Roche Diagnostics Corporation, Indianapolis, Ind., USA; "Sakura" is Sakura Finetek USA, Inc., Torrance, Calif., USA; "Santa Cruz" is Santa Cruz Biotechnology, Inc., Santa Cruz, Calif., USA; and, "Sigma" is Sigma-Aldrich Corporation, Saint Louis, Mo., USA.

1. General Methods a. Determination of Human Muscle Atrophy Signatures 1 and 2.

Human muscle atrophy signatures 1 and 2 were determined as previously described in Kunkel, S. D., et al. ((2011) *Cell metabolism* 13, 627-638).

b. Mouse Protocols.

Male C57BL/6 mice, ages 6-8 weeks, were obtained from NCI, housed in colony cages with 12 h light/12 h dark cycles. Mice were used for experiments within 3 weeks of their arrival. Unless otherwise indicated, mice were maintained on standard chow (Harlan; Teklad Diet, Formula 7013, NIH-31 Modified Open Formula Mouse/Rat Sterilizable Diet). Ursolic acid and tomatidine (Enzo Life Sciences) were prepared as suspensions in corn oil (for i.p. injections); alternatively, the ursolic acid and tomatidine were added directly to standard chow (Harlan; Teklad Diet, Formula 7013) or standard high fat diet (Harlan; Teklad Diet, Formula TD.93075) as a customized chow. Mice were fasted by removing food, but not water, for 24 hours. Unilateral TA muscle immobilization was performed under isoflurane anesthesia using an Autosuture Royal 35W skinstapler (Tyco Healthcare, Point Claire, QC, Canada) as described previously by Ebert S M, et al., (J. Biol. Chem. 287: 27290-27301, 2012).

Fasting blood glucose levels were obtained from the tail vein with an ACCU-CHEK® Aviva glucose meter (Roche Diagnostics). Forelimb grip strength was determined using a grip strength meter equipped with a triangular pull bar (Columbus Inst). Each mouse was subjected to 5 consecutive tests to obtain the peak value. Plasma leptin levels were measured by RIA at the Vanderbilt University Hormone Assay Core Facility. Plasma cholesterol, triglyceride, creatinine, bilirubin and ALT were measured using the VITROS® 350 Chemistry System (Ortho). Energy expenditure was determined as previously described by Kunkel S D, et al. (PLoS ONE. 7: e39332, 2012). NMR measurements of lean and fat mass determined with a Bruker minispec LF90II body composition analyzer. All animal procedures were approved by the Institutional Animal Care and Use Committee of the University of Iowa.

c. Histological Analysis.

Following harvest, tissues were immediately placed in isopentane that had been chilled to −160° C. with liquid $N_2$. Muscles were embedded in tissue freezing medium, and 10 μm sections from the mid-belly were prepared using a Microm HM 505 E cryostat equipped with a CryoJane sectioning system (Instrumedics). Adipose tissue was fixed in 10% neutral buffered formalin, embedded in paraffin, and then 4 μm sections were prepared using a Microm HM355 S motorized microtome (Microm). Hematoxylin and eosin stains were performed using a DRS-601 automatic slide stainer (Sakura), and examined on an Olympus IX-71 microscope equipped with a DP-70 camera. Image analysis was performed using ImageJ software (public domain, available from the National Institutes of Health, USA). Muscle fiber diameter was measured using the lesser diameter method, as described elsewhere (Dubowitz V, et al. (2007) *Muscle biopsy: a practical approach* (*Saunders* Elsevier, Philadelphia) 3rd Ed pp XIII, 611 s).

d. Measurement of Serum Ursolic Acid Levels.

Ursolic acid is extracted from serum using a 10:1 mixture of hexane:propanol (recovery >90%), and then conjugated via its carboxylic acid group to 2-(2,3-naphthalimino)ethyl trifluoromethanesulfonate (Invitrogen; Ne-OTf), a moiety that enhances TUV and fluorescence detection. Derivatized samples are then analyzed on a Waters Acquity UPLC equipped with a 100×2.1 mm C18 HSS column with 1.8 µm beads (Waters Part No. 186003533) and a TUV detector.

2. Summary of Data

These studies began with a search for pharmacologic inhibitors of skeletal muscle atrophy. Skeletal muscle atrophy is common and debilitating condition that lacks a pharmacologic therapy. To identify and develop new therapeutic approaches to this pathophysiological condition, an approach using gene expression signatures to connect small molecules, genes, and disease was used. Briefly, two unbiased mRNA expression signatures of skeletal muscle atrophy were determined (Kunkel S D, et al. *Cell Metabolism.* 13: 627-638, 2011). It was next hypothesized that pharmacologic compounds whose effects on cellular mRNA levels were opposite to muscle atrophy signatures-1 and -2 might inhibit skeletal muscle atrophy. To identify candidate compounds, the Connectivity Map (Lamb J, et al. (2006) *Science* (New York, N.Y. 313(5795):1929-1935) was used to compare muscle atrophy signatures-1 and -2 to mRNA expression signatures of >1300 bioactive small molecules. These results identified several predicted inhibitors of human skeletal muscle atrophy, including ursolic acid and tomatidine.

The predicted inhibitors of human skeletal muscle atrophy, i.e. compounds with negative connectivity with the muscle atrophy signatures, are shown in Tables 1 and 2 below. Table 1 shows compounds with negative connectivity to human muscle atrophy signature-1, whereas Table 2 shows compounds with negative connectivity to human muscle atrophy signature-2.

As a proof-of-concept of the utility of muscle atrophy signatures-1 and -2 described herein, the effects of ursolic acid were assessed in mice, and surprisingly it was discovered ursolic acid inhibited muscle atrophy and also promoted muscle hypertrophy and reduced adiposity as shown by Kunkel, S. D., et al. ((2011) *Cell metabolism* 13, 627-638). Further studies showed that urslic acid also reduced diet-induced obesity, pre-diabetes and fatty liver disease as shown by Kunkel S. D., et al. (PLoS ONE. 7: e39332, 2012). Some of these ursolic acid data are described in greater detail below. Thereafter, it is shown that tomatidine, like ursolic acid, reduces muscle atrophy, stimulates muscle hypertrophy and reduces adiposity and diet-induced obesity.

TABLE 1

Compounds with negative connectivity to human muscle atrophy signature-1.

| Cmap name/cell line | Connectivity score | n | Enrichment | p | Specificity | % Non-null |
|---|---|---|---|---|---|---|
| conessine - HL60 | −0.752 | 1 | −0.991 | — | — | 100 |
| allantoin - HL60 | −0.622 | 1 | −0.954 | — | — | 100 |
| conessine - PC3 | −0.598 | 1 | −0.941 | — | — | 100 |
| tacrine - HL60 | −0.551 | 1 | −0.91 | — | — | 100 |
| tomatidine - HL60 | −0.497 | 1 | −0.873 | — | — | 100 |
| tomatidine - PC3 | −0.483 | 1 | −0.861 | — | — | 100 |
| naringenin - PC3 | −0.462 | 1 | −0.846 | — | — | 100 |
| allantoin - MCF7 | −0.347 | 2 | −0.735 | 0.13873 | 0.1118 | 50 |
| tomatidine - MCF7 | −0.343 | 2 | −0.78 | 0.09489 | 0.2263 | 50 |
| naringenin - MCF7 | −0.219 | 2 | −0.546 | 0.4127 | 0.6589 | 50 |
| allantoin - PC3 | −0.077 | 2 | −0.414 | 0.78446 | 0.7654 | 50 |

TABLE 2

Compounds with negative connectivity to human muscle atrophy signature-2.

| Cmap name/cell line | Connectivity score | n | Enrichment | p | Specificity | % Non-null |
|---|---|---|---|---|---|---|
| tacrine - HL60 | −0.870 | 1 | −0.998 | — | — | 100 |
| tomatidine - PC3 | −0.861 | 1 | −0.998 | — | — | 100 |
| naringenin - PC3 | −0.754 | 1 | −0.990 | — | — | 100 |
| betulinic acid - HL60 | −0.569 | 1 | −0.929 | — | — | 100 |
| conessine - HL60 | −0.543 | 1 | −0.915 | — | — | 100 |
| allantoin - MCF7 | −0.486 | 2 | −0.840 | 0.05114 | 0.04710 | 100 |
| naringenin - MCF7 | −0.314 | 2 | −0.460 | 0.64871 | 0.84500 | 50 |
| tomatidine - MCF7 | −0.281 | 2 | −0.611 | 0.30586 | 0.65260 | 50 |
| tomatidine - HL60 | −0.763 | 1 | −0.991 | — | — | 100 |

3. Ursolic Acid Induces Skeletal Muscle Hypertrophy.

The results that ursolic acid reduced muscle atrophy, suggested the hypothesis that ursolic acid might promote muscle hypertrophy in the absence of an atrophy-inducing stress was reasonable. Mice were provided ad lib access to either standard chow (control diet) or standard chow supplemented with 0.27% ursolic acid (ursolic acid diet) for 5 weeks before grip strength was measured and tissues were harvested. After five weeks, mice administered ursolic had increased lower hindlimb muscle weight, quadriceps weight, and upper forelimb muscle (triceps and biceps) weight.

Moreover, dietary ursolic acid increased the specific force generated by muscles ex vivo. Briefly, six-week old male C57BL/6 mice were provided either standard diet or diet containing 0.27% ursolic acid for 16 weeks before being euthanized. The lower hindlimb was removed (by transecting the upper hindlimb mid-way through the femur), and placed in Krebs solution aerated with 95% $O_2$ and 5% $CO_2$. The gastrocnemius, soleus and tibialis anterior muscles, as well as the distal half of the tibia and fibula were then removed and discarded, leaving the extensor digitorum longus and peroneus muscles with their origins and insertions intact. A suture was placed through the proximal tendon and secured to the distal femur fragment. This ex vivo preparation was then mounted vertically in a water jacket bath (Aurora Scientific 1200A Intact Muscle Test System, filled with aerated Krebs solution) by attaching the suture to a servo-controlled lever (superiorly) and clamping the metatarsals (inferiorly). Passive muscle force was adjusted to a baseline of 1 g, and then muscles were stimulated with supramaximal voltage (80 V) at 100 Hz. The mean time from euthanasia to maximal force measurements was 10 min. After force measurements, muscles were removed and weighed in order to calculate specific titanic force. Data are means±SEM from 5-6 mice per diet. P-values were determined with a t-test. Together, the data provide morphological and functional evidence that ursolic acid induced skeletal muscle hypertrophy.

4. Ursolic Acid Reduces Adiposity.

Mice were provided ad lib access to standard chow supplemented with the indicated concentration (weight percent in chow, either 0.14% or 0.28%) of ursolic acid for 7 weeks before tissues were harvested for analysis. Data are means±SEM from 10 mice per diet. Data for the effects of ursolic acid on weights of skeletal muscle (quadriceps+triceps), epididymal fat, retroperitoneal fat and heart show that 7 weeks of dietary ursolic acid increased skeletal muscle weight in a dose-dependent manner, with a peak effect at 0.14% ursolic acid. Interestingly, although ursolic acid increased muscle weight, it did not increase total body weight (P-values were 0.71 and 0.80 for initial and final weights, respectively).

The data also show that 7 weeks of dietary ursolic acid reduced the weight of epididymal and retroperitoneal fat depots, with a peak effect at 0.14%. In another study, mice were provided ad lib access to either standard chow (control diet) or standard chow supplemented with 0.27% ursolic acid (ursolic acid diet) for 5 weeks. The relationship between skeletal muscle weight (quadriceps, triceps, biceps, TA, gastrocnemius and soleus) and retroperitoneal adipose weight show that 5 weeks of ursolic acid administration (0.14%) also reduced adipose weight. Thus, muscle and fat weights were inversely related. Without wishing to be bound by a particular theory, ursolic acid-treated mice contain less fat because, in part, ursolic acid increases skeletal muscle Akt activity (Kunkel S. D., et al. *Cell Metabolism.* 13: 627-638, 2011.), and muscle-specific increases in Akt activity reduce adiposity as a secondary consequence of muscle hypertrophy (Lai K M, et al. (2004) *Molecular and cellular biology* 24(21):9295-9304; Izumiya Y, et al. (2008) *Cell metabolism* 7(2):159-172).

Ursolic acid reduced adipose weight by reducing adipocyte size. The changes in adipocyte size were accompanied by a significant reduction in plasma leptin levels, which correlated closely with adipose weight. Importantly, ursolic acid also significantly reduced plasma triglyceride and cholesterol. Although ursolic acid reduced leptin, it did not alter food intake. In this study, mice were provided ad lib access to either standard chow (control diet) or standard chow supplemented with 0.27% ursolic acid (ursolic acid diet) for 4 weeks. Mice were then moved to a comprehensive animal metabolic monitoring system (CLAMS; Columbus Instruments, Columbus, Ohio) and provided with ad lib access to the same diets. Food consumption was measured for 48 hours. Data are means±SEM from 6 mice per group. However, ursolic acid did not alter weights of heart, liver or kidney, nor did it elevate plasma markers of hepatotoxicity or nephrotoxicity (alanine aminotransferase, bilirubin and creatinine). The data were obtained as follows: mice were provided ad lib access to either standard chow (control diet) or standard chow supplemented with 0.27% ursolic acid (ursolic acid diet) for 5 weeks before tissues and plasma were harvested for the indicated measurements; each data point represents one mouse, and horizontal bars denote the means. Thus, dietary ursolic acid had two major effects: skeletal muscle hypertrophy and reduced adiposity.

5. Ursolic Acid Reduces Weight Gain and White Adipose Tissue.

The findings that ursolic acid increased skeletal muscle and decreased adiposity suggested that ursolic acid might increase energy expenditure, which would lead to obesity resistance. To test this, C57BL/6 mice were given ad libitum access to a high fat diet (HFD; Teklad TD.93075; 55% calories from fat) lacking or containing 0.27% ursolic acid. After 7 weeks, mice from each group were studied for three days in comprehensive lab animal monitoring systems ("CLAMS"; Columbus Instruments). In the CLAMS, mice were maintained on the same diet they had been eating since the beginning of the experiment. Following CLAMS, tissues were harvested for analysis. In high fat-fed mice, ursolic acid dramatically reduced weight gain, and this effect was apparent within one week. As previously observed in mice fed ursolic acid and standard chow, ursolic acid increased grip strength and muscle mass. Moreover, ursolic acid reduced retroperitoneal and epididymal fat. Interestingly, in the scapular fat pad, which contains a mixture of white and thermogenic brown fat, ursolic acid reduced white fat, but increased brown fat. Importantly, increased skeletal muscle and brown adipose tissue would be predicted to increase energy expenditure. Indeed, CLAMS revealed that ursolic acid increased energy expenditure, providing an explanation for how ursolic acid reduces adiposity and obesity. Remarkably, CLAMS analysis revealed that ursolic acid-treated mice consumed more food, even though they gained less weight.

6. Ursolic Acid Reduces Obesity-Related Pre-Diabetes, Diabetes, Fatty Liver Disease and Hypercholesterolemia.

The study was carried out as follows: C57BL/6 mice were given ad libitum access to a high fat diet ("HFD"; Teklad TD.93075; 55% calories from fat) lacking or containing 0.27% ursolic acid. After 5 weeks, mice were fasted for 16 h before blood glucose was measured via the tail vein. Normal fasting blood glucose: ≤100 mg/dl. (B-I) After 7 weeks, liver and plasma were harvested for analysis. The data suggest that most mice fed HFD without ursolic acid for 6 weeks developed impaired fasting glucose (pre-diabetes) or diabetes. Importantly, this was prevented by ursolic acid. In addition, mice fed HFD without ursolic acid developed fatty liver disease, as evidenced by increased liver weight (>30% increase above normal mouse liver weight of 1500 mg), hepatocellular lipid accumulation, and elevated plasma liver function tests. However, ursolic acid prevented all of these hepatic changes. In addition, ursolic acid reduced obesity-related hypercholesterolemia.

7. Ursolic Acid Serum Levels Associated with Increased Muscle Mass and Decreased Adiposity.

To determine the dose-response relationship between dietary ursolic acid and muscle and adipose weight, C57BL/6 mice were fed standard chow containing varying amounts of ursolic acid for 7 weeks. Serum ursolic acid levels from mice were determined as described above. As shown previously, ursolic acid increased skeletal muscle weight and decreased weight of retroperitoneal and epididymal fat pads in a dose-dependent manner, but did not alter heart weight. These effects of ursolic acid were discernable at 0.035% ursolic acid and were maximal at doses ≥0.14% ursolic acid. Serum was collected from these same mice at the time of necropsy, and then measured random serum ursolic acid levels via ultra-high performance liquid chromatography (UPLC). The data indicate that ursolic acid serum levels in the range of 0.25-0.5 μg/ml are sufficient to increase muscle mass and decrease adiposity. Of note, 0.5 μg/ml equals 1.1 μM ursolic acid, close to the dose used in the Connectivity Map (8.8 μM) and in the C2C12 experiments (10 μM) described above.

8. Tomatidine Reduces Fasting-Induced Skeletal Muscle Atrophy

Tomatidine has the following structure:

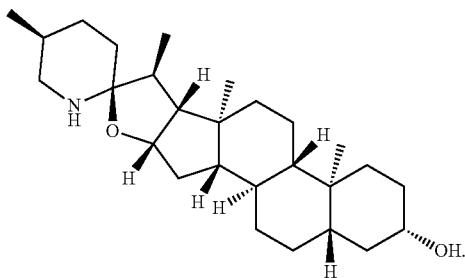 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

Figure 2:
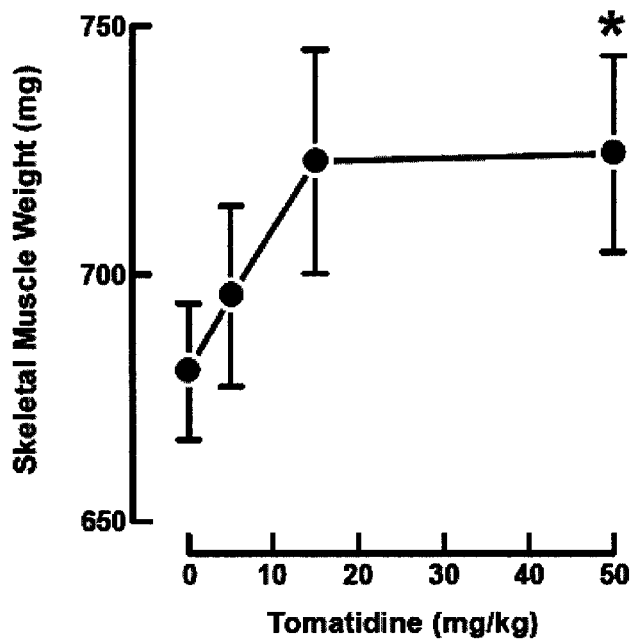
FIG. 2 is a graph of mouse skeletal muscle weight as a function of tomatidine dosage.
Figure 3:
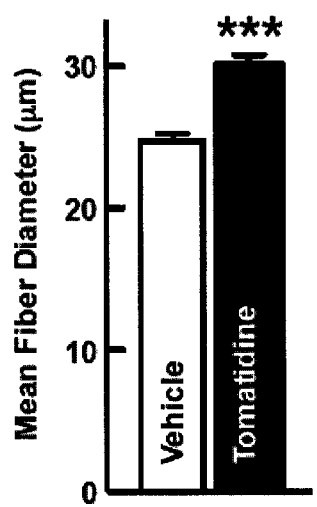
FIG. 3 is a bar graph of mouse skeletal muscle fiber diameter for control and for tomatidine at 50 mg/kg.
Figure 4:
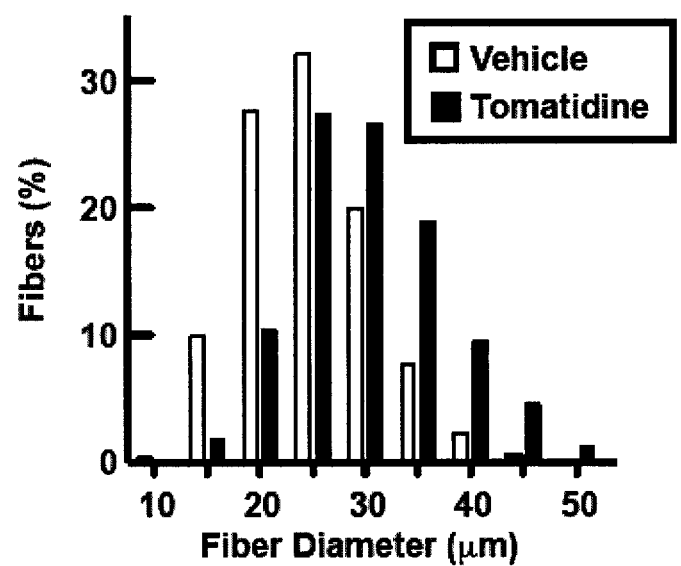
FIG. 4 is a graph showing distribution of percentage of mouse skeletal muscle fibers as a function of fiber diameter for control and for tomatidine at 50 mg/kg.

The mRNA expression signature of tomatidine negatively correlated to muscle atrophy signature-1 (Table 1) and muscle atrophy signature-2 (Table 2). Therefore tomatidine could inhibit skeletal muscle atrophy. To test this, food was withdrawn from mice, and then vehicle, ursolic acid (200 mg/kg) or tomatidine (50 mg/kg) were administered by i.p. injection. Twelve hours later, mice received another i.p. injection of vehicle or the same dose of ursolic acid or tomatidine. Twelve hours later, skeletal muscles were harvested and weighed. Both ursolic acid and tomatidine increased skeletal muscle, indicating decreased fasting-induced skeletal muscle atrophy (FIG. 1). We next used the same protocol to compare the effects of vehicle (corn oil) and tomatidine (5, 15 and 50 mg/kg). Tomatidine reduced muscle atrophy in a dose-dependent manner, with maximal effect at 50 mg/kg and EC50 between 5 and 15 mg/kg (FIG. 2). Moreover, tomatidine increased the size of skeletal muscle fibers in fasted muscles (FIGS. 3 and 4), indicating reduced muscle atrophy. Data in FIG. 1 are mean skeletal muscle weight±SEM from ≥9 mice per condition; *P<0.05 by unpaired t-test. Data in FIG. 2 are mean skeletal muscle weight±SEM from ≥11 mice per condition; *P<0.05 by unpaired t-test. In FIGS. 1 and 2 skeletal muscle weight represents the combined weights of bilateral quadriceps, tibialis anterior, gastrocnemius and soleus muscles. Data in FIG. 3 are mean fiber diameters±SEM from TA muscles of ≥4 fasted mice per condition; ***P<0.0001 by unpaired t-test. Data in FIG. 4 are size distributions of fibers from FIG. 3 (≥650 fibers per condition). Tomatidine was obtained from Enzo Life Sciences. Taken together, these data indicate that tomatidine reduces fasting-induced skeletal muscle atrophy.

Figure 5:
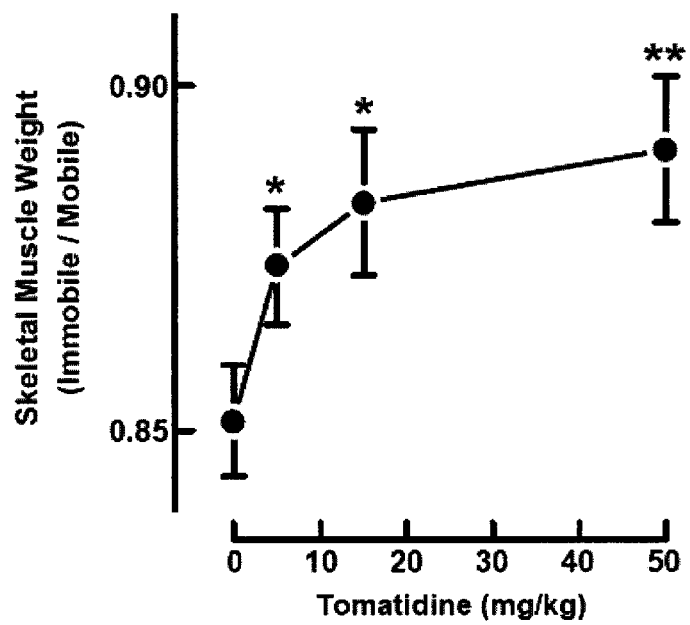
FIG. 5 is a graph of mouse skeletal muscle weight as a function of tomatidine dosage.
Figure 6:
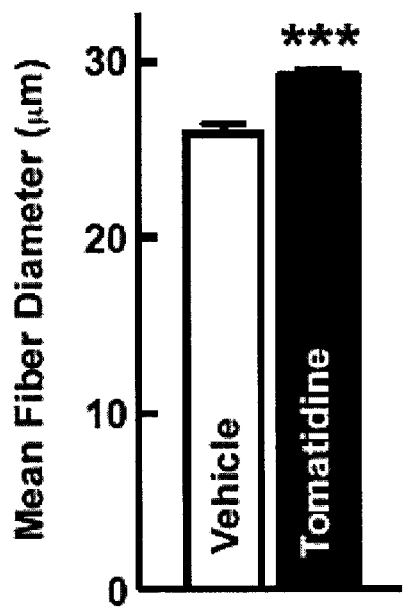
FIG. 6 is a bar graph of mouse skeletal muscle fiber diameter for control and for tomatidine at 15 mg/kg.
Figure 7:
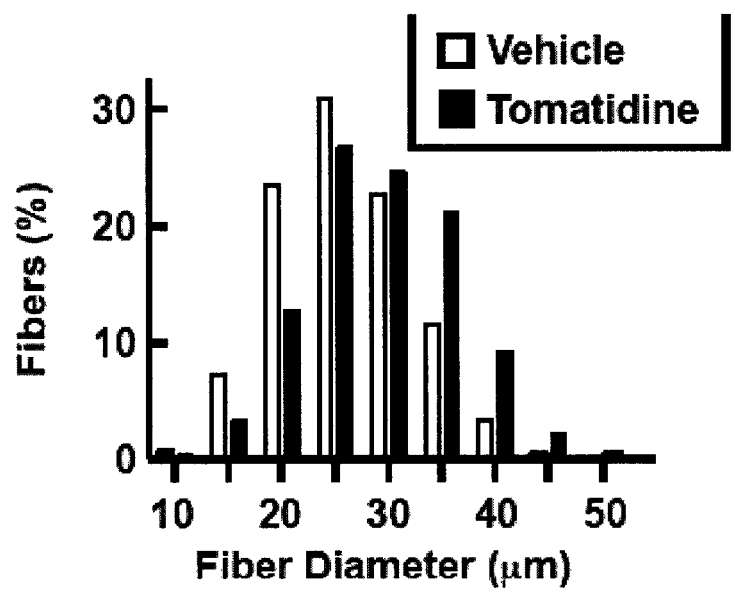
FIG. 7 is a graph showing distribution of percentage of mouse skeletal muscle fibers as a function of fiber diameter for control and for tomatidine at 15 mg/kg.

9. Tomatidine Reduces Immobilization-Induced Skeletal Muscle Atrophy and Enhances Recovery from Immobilization-Induced Skeletal Muscle Atrophy To test whether tomatidine can reduce skeletal muscle atrophy in immobilized muscles, mice were given i.p. injections of vehicle (corn oil) or tomatidine (5, 15 or 50 mg/kg) twice a day beginning on day 0. On day 2, the left tibialis anterior (TA) muscle of each mouse was immobilized using an Autosuture Royal 35W skin stapler to induce skeletal muscle atrophy. During immobilization, vehicle or the same doses of tomatidine continued to be administered via i.p. injection twice daily, and the right TA remained mobile and served as an intrasubject control. On day 8, bilateral TA muscles were harvested and weighed. In each mouse, the left (immobile) TA weight was normalized to the right (mobile) TA weight. Tomatidine reduced muscle atrophy in a dose-dependent manner, with maximal effect at 50 mg/kg and EC50<5 mg/kg (FIG. 5). Moreover, tomatidine increased the size of skeletal muscle fibers in immobilized muscles (FIGS. 6 and 7), indicating reduced muscle atrophy. Data in FIG. 5 are means±SEM from ≥11 mice per condition; *P<0.05 and P<0.01 by unpaired t-test. Data in FIG. 6 are mean fiber diameters±SEM from 4 immobilized TA muscles per condition; *P<0.001 by unpaired t-test. Data in FIG. 7 are fiber size distributions of ≥1500 fibers from 4 immobilized TA muscles per condition. Collectively, these data indicate that tomatidine reduces immobilization-induced muscle atrophy.

Figure 8:
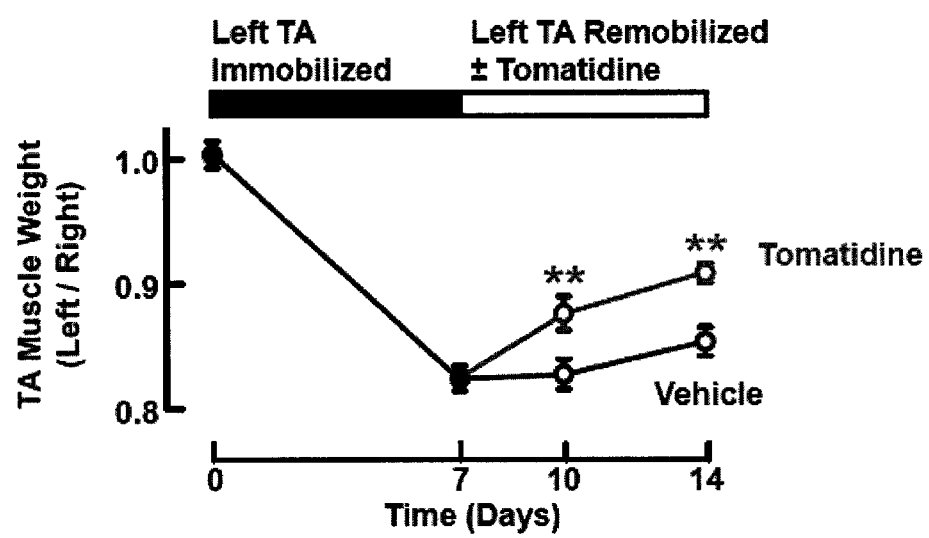
FIG. 8 is a graph of mouse skeletal muscle weight as a function of time for control and for tomatidine at 25 mg/kg.

To determine whether tomatidine might enhance recovery from skeletal muscle atrophy, mouse TA muscles were immobilized for 7 days to induce atrophy (FIG. 8). Muscles were then remobilized by removing the staple from the left TA muscle. Treatment with vehicle or tomatidine (25 mg/kg) was then initiated. Both vehicle and tomatidine were given via i.p. injection twice daily. Tomatidine significantly enhanced the recovery of skeletal muscle mass. Data in FIG. 8 are means±SEM from 8 mice per condition; **P<0.01 by unpaired t-test. Taken together, these data indicate that tomatidine is effective as both a prevention and treatment for skeletal muscle atrophy.

10. Tomatidine Stimulates Skeletal Muscle Hypertrophy and Reduces Adiposity in Non-Obese Mice The finding that tomatidine reduces skeletal muscle atrophy suggested that tomatidine might stimulate skeletal muscle hypertrophy. To test this, age- and weight-matched 6-8 week old male C57BL/6 mice were obtained from the National Cancer Institute. Upon arrival, baseline body composition was measured by NMR using a Bruker minispec LF90$_{\text{II}}$ instrument. One week later, cages of mice were randomized to receive ad libitum access to either standard chow (Harlan Teklad formula 7013) or standard chow supplemented with 0.05% tomatidine. Over the next 5 weeks, body weight and food intake per cage were measured weekly. After 5 weeks in the absence or presence of tomatidine treatment, forelimb grip strength was determined using a grip strength meter (Columbus Instruments) and body composition was re-analyzed by NMR. Mice were then euthanized and skeletal muscles (bilateral triceps, quadriceps, TA, gastrocnemius and soleus) and fat pads (retroperitoneal, scapular, and epididymal) were harvested and weighed. Histologic sections of TA muscles were prepared for fiber size analysis.

Figure 9:
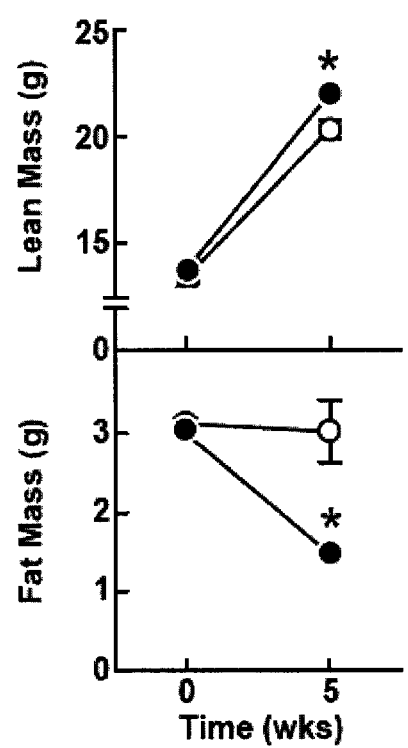
FIG. 9 is a graph of fat mass and lean mass (in grams) for mouse skeletal muscle as a function of time for control mice and for mice given tomatidine at 0.05% in the diet.

Tomatidine did not significantly alter total body weight or food intake. However, NMR body composition analysis demonstrated that tomatidine significantly increased lean mass and decreased fat mass (FIG. 9). Data in FIG. 9 are means −/+SEM from 16 mice per condition; *P<0.05. P-values were determined with unpaired t-tests. Increased lean mass was consistent with skeletal muscle hypertrophy, whereas decreased fat mass indicated reduced adiposity.

Figure 10:
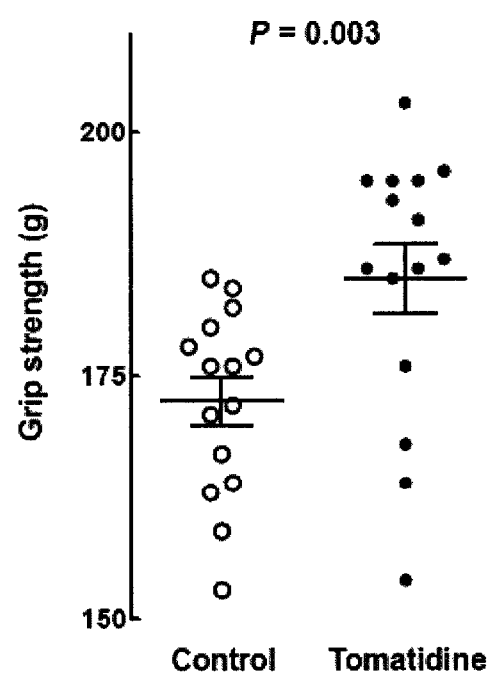
FIG. 10 is a scatter plot showing grip strength for fifteen individual mice in each of two test groups: control mice and mice given tomatidine at 0.05% in the diet; the horizontal bars denote the mean±SEM.

Consistent with skeletal muscle hypertrophy, tomatidine significantly increased grip strength (FIG. 10), as well as the weights of triceps, quadriceps, TA, gastrocnemius and soleus muscles and the sum total weight of these skeletal muscles. Moreover, tomatidine increased the size of skeletal muscle fibers. In FIG. 10, each data point represents one mouse and the horizontal bars denote the means −/+SEM from 15 mice per condition. Taken together, these data indicate that tomatidine stimulates skeletal muscle hypertrophy.

In contrast to its effects on skeletal muscle, tomatidine decreased the weight of retroperitoneal, scapular, and epididymal fat pads and the sum total weight of these fat pads. These data are consistent with the finding that tomatidine reduced fat mass by NMR. Taken together, these data indicate that tomatidine reduces adiposity in non-obese mice.

There was a significant negative correlation between fat weight and skeletal muscle weight. Skeletal muscle weight represents the combined weights of bilateral triceps, quadriceps, tibialis anterior, gastrocnemius, and soleus muscles. Fat weight represents the combined weights of bilateral epididymal, retroperitoneal and scapular fat pads. Coupled with the findings that tomatidine stimulates muscle hypertrophy and decreases adiposity, these data indicate that tomatidine increases the ratio of skeletal muscle to fat.

11. Tomatidine Stimulates Skeletal Muscle Hypertrophy and Reduces Adiposity and Obesity in Diet-Induced Mice The findings that tomatidine increased skeletal muscle and decreased adiposity in non-obese mice suggested that tomatidine might increase muscle and reduce adiposity and obesity in diet-induced obese mice. To test this, age- and weight-matched 6-8 wk old male C57BL/6 mice were obtained from the National Cancer Institute and randomized to receive ad libitum access to either high fat diet ("HFD," Harlan Teklad formula TD.93075) or HFD supplemented with 0.05% tomatidine. Over the next 6 weeks, body weight and food intake per cage were measured weekly. After 6 weeks in the absence or presence of tomatidine treatment, forelimb grip strength was determined using a grip strength meter (Columbus Instruments). Mice were then euthanized and skeletal muscles (bilateral triceps, quadriceps, TA, gastrocnemius and soleus) and fat pads (retroperitoneal, scapular, and epididymal) were harvested and weighed.

As expected, HFD markedly increased total body weight and induced obesity in both groups of mice. However, tomatidine significantly reduced the amount of weight gain. In addition, tomatidine significantly increased food intake. These data indicate that tomatidine reduces obesity. Moreover, the findings that tomatidine decreased weight gain but increased food intake suggest that tomatidine reduces weight gain by increasing energy expenditure. A potential mechanism of increased energy expenditure is increased skeletal muscle mass.

Although tomatidine reduced weight gain, it significantly increased grip strength, as well as the weights of triceps, quadriceps, TA, gastrocnemius and soleus muscles and the sum total weight of these skeletal muscles. Taken together, these data indicate that tomatidine stimulates skeletal muscle hypertrophy in obese mice.

Figure 11:
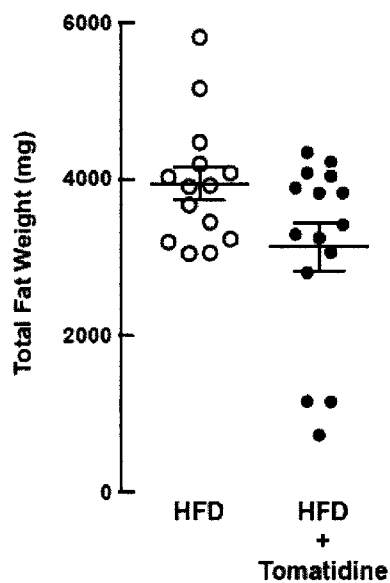
FIG. 11 is a scatter plot showing total fat weight for individual mice in each of two test groups maintained on a high fat diet: control mice and mice given tomatidine at 0.05% in the diet; the horizontal bars denote the mean±SEM.

In contrast to its effects on skeletal muscle, tomatidine decreased the weight of retroperitoneal, scapular, and epididymal fat pads and the sum total weight of these fat pads (FIG. 11). In FIG. 11, each data point represents one mouse and the horizontal bars denote the means −/+SEM from ≥14 mice per condition. P-values were determined with unpaired t-tests. Taken together, these data indicate that tomatidine reduces adiposity in obese mice.

There was a significant negative correlation between fat weight and skeletal muscle weight. Skeletal muscle weight represents the combined weights of bilateral triceps, quadriceps, tibialis anterior, gastrocnemius, and soleus muscles. Fat weight represents the combined weights of bilateral epididymal, retroperitoneal and scapular fat pads. Coupled with the findings that tomatidine stimulates muscle hypertrophy and decreases adiposity, these data indicate that tomatidine increases the ratio of skeletal muscle to fat in obese mice.

12. Tomatidine Stimulates Protein Accretion and Hypertrophy in Cultured Skeletal Myotubes The finding that tomatidine stimulated skeletal muscle hypertrophy in vivo suggested that tomatidine might have similar effects in a well-established in vitro model of skeletal muscle: fully differentiated, post-mitotic C2C12 skeletal myotubes. To test this, mouse C2C12 myoblasts were obtained from ATCC (CRL-1772) and maintained at 37° C. and 5% $CO_2$ in Dulbecco's modified Eagle's medium (ATCC #30-2002) containing antibiotics (100 units/ml penicillin, 100 mg/ml streptomycin sulfate) and 10% (v/v) fetal bovine serum (FBS). Myoblasts were set up for experiments on day 0 in 6-well plates at a density of $2.5 \times 10^5$ cells/well. On day 2, myoblasts were induced to differentiate into myotubes by replacing 10% FBS with 2% horse serum (HS). On day 7, myotubes were rinsed once with PBS, and then 2% HS was replaced with 10% FBS. The vehicle (0.1% DMSO) or varying concentrations of tomatidine were added directly to the media. After 48 h incubation, myotube protein content and size were measured.

To determine myotube protein content, myotubes were washed with ice cold PBS, scraped into lysis buffer (10 mM Tris-HCl, pH 7.6, 100 mM NaCl, and 1% (w/v) SDS, complete Mini protease inhibitor cocktail (Roche), and a 1:100 dilution of phosphatase inhibitor cocktail 3 (Sigma)), and then lysed with 10 passes through a 22-gauge needle. An aliquot of each myotube lysate sample was then used to determine protein concentration by the BCA kit (Pierce). Tomatidine significantly increased total cellular protein in a dose-dependent manner, indicating myotube hypertrophy. To determine myotube size, myotubes were subjected to immunofluorescence staining with anti-troponin primary antibody and a fluorescent secondary antibody. Myotubes were then imaged on an Olympus IX-71 microscope equipped with a DP-70 camera and epifluorescence filters. Image analysis was performed using ImageJ software. Tomatidine increased myotube diameter in a dose-dependent manner, indicating myotube hypertrophy. Taken together, these data indicate that tomatidine stimulates skeletal myotube hypertrophy in vitro. In addition, these data indicate that tomatidine directly affects skeletal muscle cells, as opposed to a secondary effect arising from non-muscle tissues.

13. Tomatidine Stimulates Protein Accretion and Hypertrophy in Cultured Skeletal Myotubes from Human To determine if tomatidine might promote growth of human skeletal muscle cells, primary human skeletal myotubes were incubated with varying concentrations of tomatidine, and then total cellular protein was measured. Primary human skeletal myoblasts, obtained from Lonza, were set-up in 6-well plates at a density of $1 \times 10^5$ cells/well. On day 2, myoblasts were induced to differentiate into myotubes by replacing 10% fetal bovine serum (FBS) with 2% horse serum (HS). On day 7, fully differentiated myotubes were incubated for 48 h with 10% FBS plus varying concentrations of tomatidine, and then harvested for quantification of total cellular protein and DNA with the Illustra TriplePrep kit (GE Healthcare). In each sample, protein was normalized to the amount of DNA, which was not altered by tomatidine. Submicromolar concentrations of tomatidine significantly increased human myotube protein in a dose-dependent manner. Data are means±SEM from 9 samples per condition. $P \le 0.01$; *$P \le 0.001$.

To determine if tomatidine stimulates cellular hypertrophy in human skeletal myotubes, fully differentiated human skeletal myotubes were incubated for 48 h with 10% FBS plus either vehicle (0.1% DMSO; control) or 1 μM tomatidine, and then stained with anti-troponin antibody to evaluate myotube size. For troponin staining, myotubes were washed with phosphate-buffered saline, fixed in 4% paraformaldehyde, permeabilized with methanol, blocked with 5% normal goat serum, and then sequentially immunostained with anti-troponin T mouse monoclonal antibody (CT3, University of Iowa Developmental Studies Hydridoma Bank) and goat anti-mouse antibody conjugated to Alexa Fluor 488. Myotubes were imaged an Olympus IX71 microscope equipped with a DP70 camera and epifluorescence filters. The diameter of each myotube was determined as the mean of three measurements per myotube. Tomatidine significantly increased the size of human skeletal myotubes, indicating myotube hypertrophy. Collectively, these data indicate that tomatidine stimulates protein accretion and hypertrophy in cultured skeletal myotubes from humans. These data also suggest that human muscle cells respond to tomatidine in a similar manner as mouse skeletal muscle, and provide evidence that tomatidine and tomatidine analogs may be useful in the prevention and treatment of skeletal muscle atrophy, and the stimulation of muscle hypertrophy, in humans.

14. Tomatidine Increases Anabolic Signaling, Protein Synthesis, and Mitochondria in Cultured Skeletal Myotubes To test whether tomatidine stimulates anabolic signaling, the effect of tomatidine on Akt/mTORC1 signaling was investigated. Akt/mTORC1 signaling is a key anabolic signaling pathway in skeletal muscle that increases protein synthesis, reduces muscle atrophy, and promotes muscle hypertrophy (Schiaffino et al., FEBS J. Epub Apr. 17, 2013). Fully differentiated C2C12 skeletal myotubes were switched to 10% FBS, incubated for 1 hr with vehicle (0.1% DMSO; control) or 1 μM tomatidine, and then harvested. Myotube protein extracts were prepared by scraping myotubes into lysis buffer (10 mM Tris-HCl, pH 7.6, 100 mM NaCl, and 1% (w/v) SDS, complete Mini protease inhibitor cocktail (Roche), and a 1:100 dilution of phosphatase inhibitor cocktail 2 and 3 (Sigma)). Myotubes were then lysed with 10 passes through a 22-gauge needle and centrifuged to pellet insoluble material. An aliquot of each soluble protein extract was used to determine protein concentration by the BCA method (Pierce). A separate aliquot of each protein extract was mixed with 0.25 volume of sample buffer (250 mM Tris-HCl, pH 6.8, 10% SDS, 25% glycerol, 0.2% (w/v) bromophenol blue, and 5% (w/v) 2-mercaptoethanol) and heated for 5 min at 95° C. An equal amount of protein from each sample was then subjected to SDS-PAGE and immunoblot analysis with antibodies specific for total and phosphorylated Akt, GSK-33 and p70 S6 kinase (S6K) (Cell Signaling). Tomatidine: 1) increased Akt phosphorylation (activity); 2) increased phosphorylation of GSK-3β, a key Akt substrate; and 3) increased phosphorylation of S6K, a key mTORC1 substrate.

To whether tomatidine stimulates protein synthesis, fully differentiated C2C12 skeletal myotubes were incubated for 30 h with vehicle (0.1% DMSO; control) or 1 μM tomatidine, and then the incorporation of [$^3$H]-leucine into total cellular protein was quantified to determine protein synthesis. Following incubation for 2 h with [$^3$H]-leucine, cells were washed three times with phosphate-buffered saline, fixed with 10% (w/v) trichloroacetic acid (TCA) for 10 min on ice, and then scraped and collected into microfuge tubes. Samples were then incubated at 4° C. for 1 h before centrifugation to pellet acid-insoluble protein. Pellets were washed once with 10% TCA and then dissolved in 1 M NaOH/1% sodium deoxycholate. An aliquot was used to quantify protein concentration, and another aliquot was neutralized with 8 M HCl and placed in scintillation cocktail for measurement of acid-insoluble radioactivity. Acid-insoluble radioactivity was then normalized to the amount of protein in each sample. Tomatidine significantly increased protein synthesis.

Mitochondria play an essential role in maintaining skeletal muscle mass (Romanello and Sandri, Curr. Hypertens. Rep. 12, 433-439). To test whether tomatidine increases mitochondria, fully differentiated C2C12 skeletal myotubes were incubated for 48 h with vehicle (0.1% DMSO; control) or 1 μM tomatidine, and then mitochondrial DNA was quantified. To quantify mitochondrial DNA, total cellular DNA (containing both mitochondrial and nuclear DNA) was extracted with the DNeasy Blood and Tissue Kit (Qiagen). Quantitative real-time PCR (qPCR) was then performed using primers specific for mitochondrial DNA and nuclear DNA (Menshikova et al. Am. J. Physiol. Endocrinol. Metab. 288, E818-825). qPCR reactions were performed in triplicate using a 7500 Fast Real-Time PCR System (Applied Biosystems), and then the relative amounts of mitochondrial and nuclear DNA were determined using the comparative cycle threshold (Ct) method. Tomatidine significantly increased mitochondrial DNA, indicating an increase in mitochondria. Data are means±SEM from 3 independent experiments. ***$P \le 0.001$. Taken together, these data suggest that tomatidine may reduce muscle atrophy and stimulate muscle hypertrophy by increasing skeletal muscle anabolic signaling, protein synthesis and mitochondria.

Figure 12:
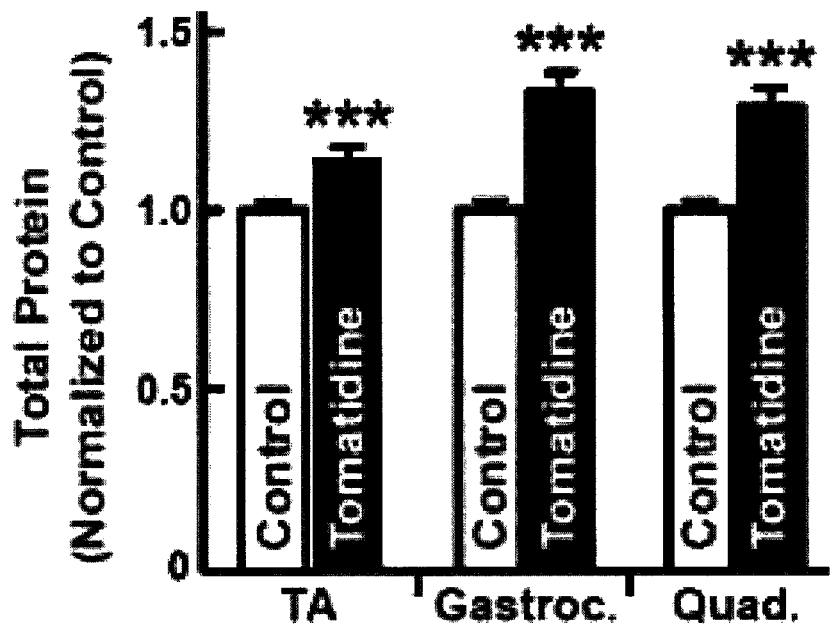
FIG. 12 is a set of three bar graphs showing total protein (normalized to control) in tibialis anterior (TA), gastrocnemius (Gastroc) and quadriceps (Quad) muscles in each of two test groups: control mice and mice given tomatidine at 0.05% in the diet.
Figure 13:
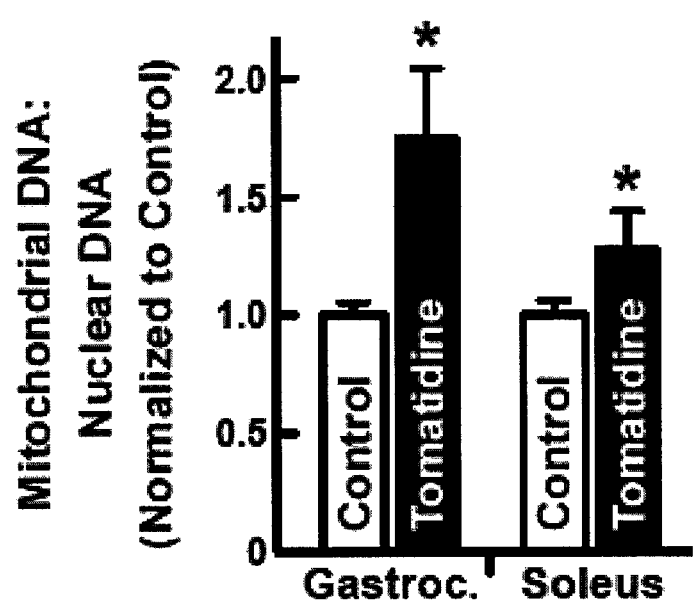
FIG. 13 is a pair of bar graphs showing the ratio of mitochondrial DNA to nuclear DNA (normalized to control) in gastrocnemius (Gastroc) and soleus muscles in each of two test groups: control mice and mice given tomatidine at 0.05% in the diet.

15. Tomatidine Increases Anabolic Signaling, Protein, and Mitochondria in Mouse Skeletal Muscle The finding that tomatidine increased anabolic signaling, protein synthesis, and mitochondria in cultured skeletal myotubes suggested that tomatidine might have similar effects in mouse skeletal muscle in vivo. To test this hypothesis, mice were fed standard chow (control) or standard chow containing 0.05% tomatidine for 5 weeks before skeletal muscles were harvested for determination of S6K phosphorylation, total cellular protein, and mitochondrial DNA. FIGS. 12 and 13 show that tomatidine significantly increased S6K phosphorylation, total cellular protein, and mitochondrial DNA in mouse skeletal muscle. Data in FIG. 12 are mean amounts of total skeletal muscle protein±SEM from 6-7 mice per condition; ***$P \le 0.001$. Data in FIG. 13 are the mean ratios of mitochondrial DNA to nuclear DNA in skeletal muscle±SEM from 6-8 mice per condition; *P≤0.05. Taken together, these data provide further evidence that tomatidine may reduce muscle atrophy and stimulate muscle hypertrophy by increasing skeletal muscle anabolic signaling, protein synthesis and mitochondria.

16. Tomatidine Increases Skeletal Muscle Specific Force

Figure 14:
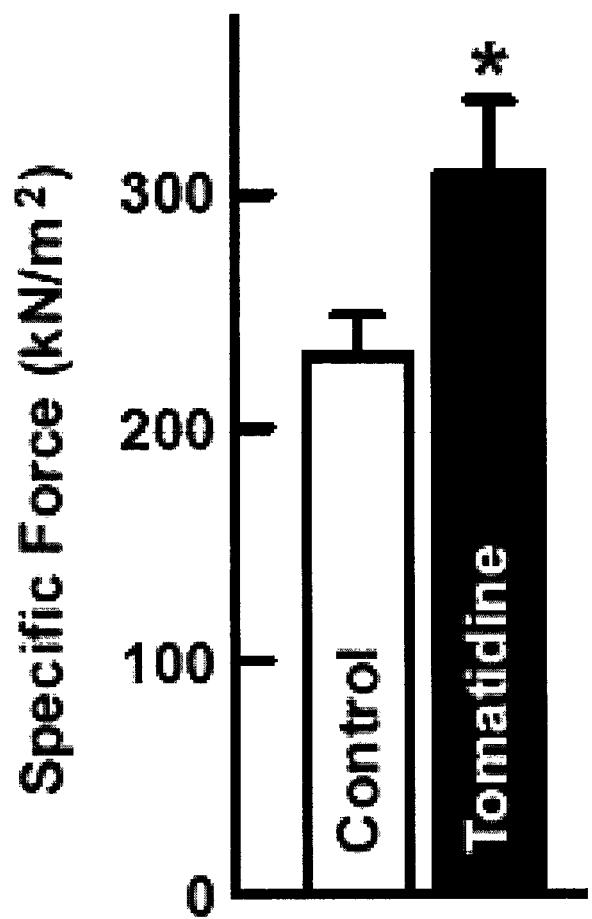
FIG. 14 is a bar graph showing specific force (in $kN/m^2$) generated by mouse extensor digitorum longus muscles ex vivo in each of two test groups: control mice and mice given tomatidine at 0.05% in the diet.

The finding that tomatidine increases grip strength (FIG. 10) suggests that tomatidine may increase skeletal muscle specific force. To test this hypothesis, mice were fed standard chow (control) or standard chow containing 0.05% tomatidine for 5 weeks. Mice were then euthanized and the lower hindlimb was removed by transecting the upper hindlimb mid-way through the femur, then placed in Krebs Ringer solution (120 mM NaCl, 23.8 mM $NaHCO_3$, 10 mM D-glucose, 4.8 mM KCl, 2.5 mM $CaCl_2$, 1.2 mM $KH_2PO_4$, 1.2 mM $MgSO_4$, 5 mM HEPES, 2.5 mM $CaCl_2$) aerated with 95% $O_2$ and 5% $CO_2$. The gastrocnemius, soleus and TA muscles, as well as the distal half of the tibia and fibula, were then removed, leaving the extensor digitorum longus muscle (EDL) with its origins and insertions intact. A staple with an attached suture was placed through the knee joint, and the preparation was mounted vertically in a water jacket bath (Aurora Scientific 1200A Intact Muscle Test System, filled with aerated Krebs-Ringer solution (95% $O_2$, 5% $CO_2$, 25° C.)) by attaching the suture to a servocontrolled lever (Model 805A; Aurora Scientific) and clamping the metatarsals inferiorly. Isometric contractile properties of the EDL muscle were evaluated according to previously methods described (Kunkel et al., *PLOS ONE* 7, e39332). To produce a maximum isometric contraction, muscles were field stimulated with supramaximal square-wave pulses (0.2 ms width) delivered to two platinum plate electrodes flanking the length of the muscle. Optimum muscle length ($L_o$) and optimum stimulation voltage were determined by micromanipulating muscle length and eliciting contractions until the peak potentiated state was reached. Maximum isometric tetanic force ($P_o$) was determined from the plateau of the tetanic curve following stimulation with supramaximal voltage (40 V) at 150 Hz with 2 min rest between recordings to prevent fatigue. Contractile measurements were recorded using a digital controller (Model 600A; Aurora Scientific) operating ASI Dynamic Muscle Control acquisition software (v4.1, Aurora Scientific). Following force testing, muscles were removed from the bath, trimmed of tendons, and weighed on an analytical balance. Optimum fiber length ($L_f$) was determined by multiplying $L_o$ by a previously determined fiber length: muscle length ratio (0.44 for the EDL muscle (Brooks and Faulkner. *J. Physiol.* 404, 71-82)). Muscle cross sectional area was determined by dividing muscle weight by the product of $L_f$ and 1.06 mg/mm$^3$ (the density of mammalian skeletal muscle (Mendez and Keys, *Metabolism: Clinical and Experimental* 9, 184-189). Muscle mass, $L_f$ and $P_o$ was then used to calculate maximum tetanic force normalized to cross-sectional area (specific force). FIG. 14 shows that tomatidine significantly increased the specific force generated by skeletal muscles. Data are means±SEM from 4 mice per condition. *P≤0.05.

17. Tomatidine Increases Exercise Capacity

Figure 15:
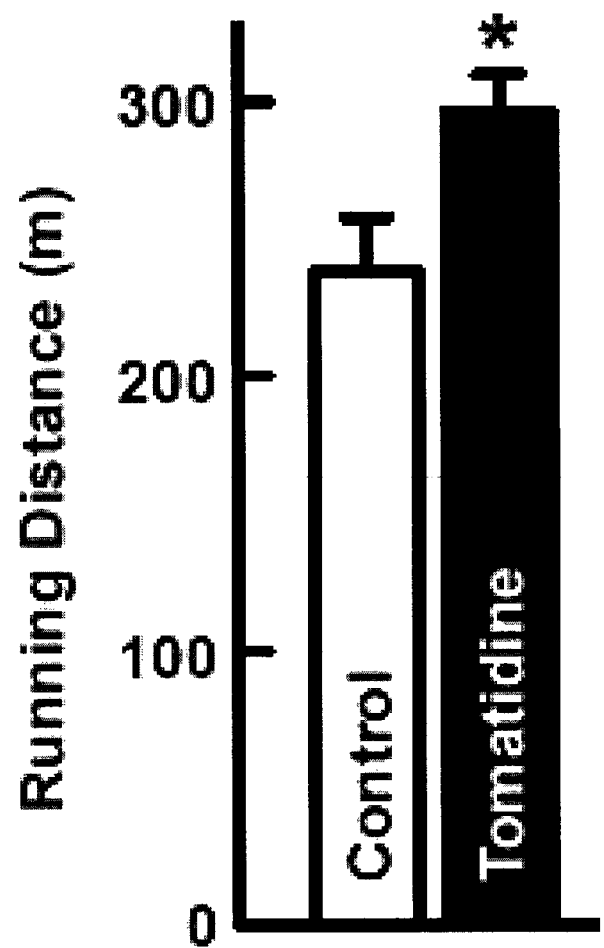
FIG. 15 is a bar graph showing distance run (in meters) in each of two test groups: control mice and mice given tomatidine at 0.05% in the diet.

To test whether tomatidine increases exercise capacity, mice were fed standard chow (control) or standard chow containing 0.05% tomatidine for 5 weeks, and then subjected to a well-established exercise treadmill protocol (Kunkel et al., *PLOS ONE* 7, e39332). For two days, mice were acclimated for 5 min a day to running on a motor-driven open treadmill with a shock grid (Columbus Instruments). During acclimation, the treadmill speed was set at 14 M/min and the treadmill incline was set at 0%. On day 3, exercise tolerance was tested: the shock grid was set at 0.2 mA, and the treadmill incline was set at 10%. For the first 5 min of testing, treadmill speed was set at 10 M/min. Every 2 min thereafter, the treadmill speed was increased by 2 M/min. Running was terminated when mice contacted the shock grid for 10 seconds. FIG. 15 shows that tomatidine significantly increased the distance run by mice on the accelerating treadmill. Data are mean distances run±SEM from 16 mice per condition. *P≤0.05. These data indicate that, in addition to increasing strength, tomatidine increases exercise capacity.

18. Tomatidine Stimulates Skeletal Muscle Hypertrophy in Old Mice

The aforementioned mouse studies utilized young (approximately 2-month-old) mice. To test whether tomatidine also stimulates skeletal muscle hypertrophy in old mice, 14-month-old C57BL/6 mice were provided ad libitum access to standard chow (control) or standard chow containing 0.05% tomatidine for 9 weeks before skeletal muscles were harvested for determination of muscle weights and muscle fiber size. Tomatidine significantly increased the weight of tibialis anterior, gastrocnemius, soleus, quadriceps, and triceps muscles. Data are means±SEM from 11 mice per condition. *P≤0.05; P≤0.01; *P≤0.001. Tomatidine also significantly increased the size of muscle fibers, indicating skeletal muscle hypertrophy. These data, coupled with the data from young mice, indicate that tomatidine stimulates skeletal muscle hypertrophy in both young and old mice.

All of the compositions and/or methods disclosed and claimed herein can be made and executed without undue experimentation in light of the present disclosure. It will be apparent to those skilled in the art that various modifications and variations can be made in the present invention without departing from the scope or spirit of the invention. More specifically, certain agents which are both chemically and physiologically related can be substituted for the agents described herein while the same or similar results can be achieved. All such similar substitutes and modifications apparent to those skilled in the art are deemed to be within the spirit, scope and concept of the invention as defined by the appended claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

19. Prophetic Synthesis of Tomatidine and Analogs

The formulas disclosed herein could be synthesized by the method disclosed by Uhle, and Moore, *J. Am. Chem. Soc.* 76, 6412 (1954); Uhle, *J. Am. Chem. Soc.* 83, 1460 (1961); and Kessar et al., *Tetrahedron* 27, 2869 (1971), which are all hereby incorporated by reference in their entirety. The disclosed compounds can also be made as shown in Scheme 5A.

SCHEME 5A

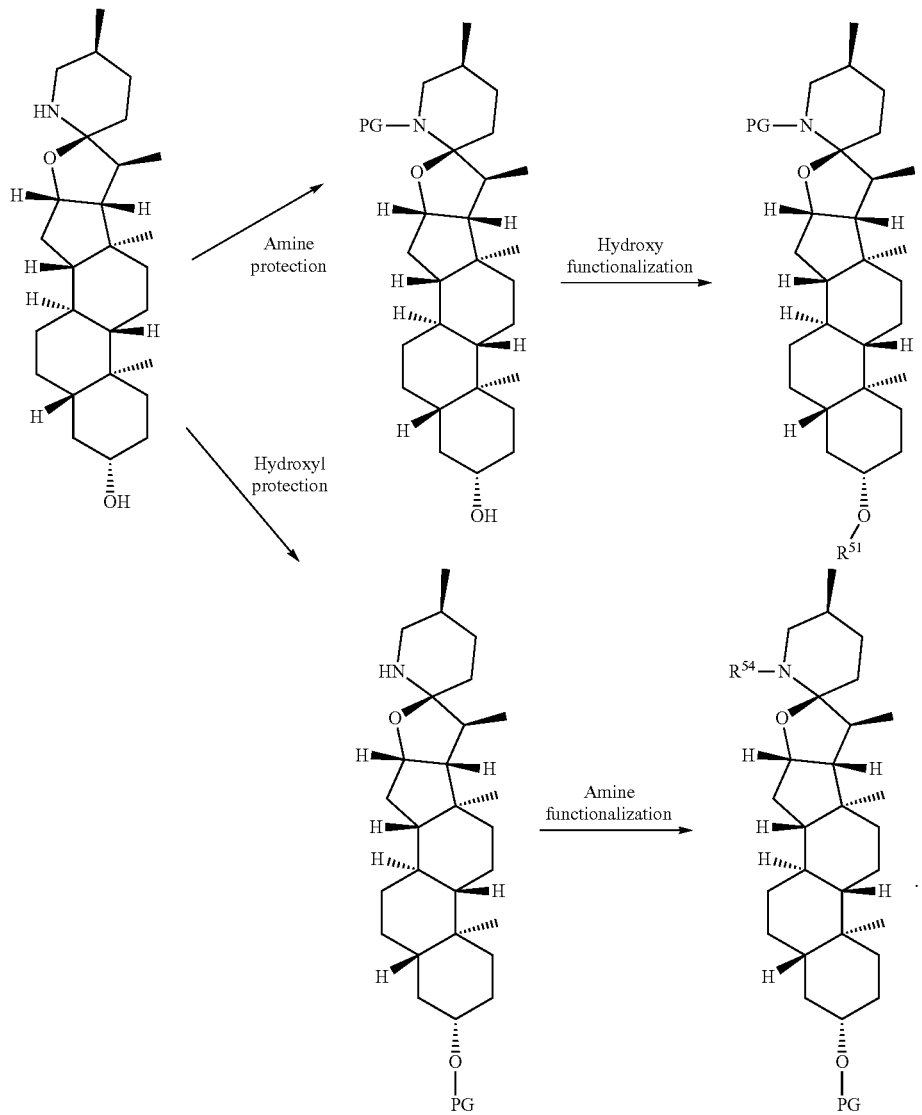

F. References

The following references, to the extent that they provide exemplary procedural or other details supplementary to those set forth herein, are specifically incorporated herein by reference.

Abellan van Kan, G. (2009) *The journal of nutrition, health & aging* 13, 708-712

Acharyya S, et al. (2005) Dystrophin glycoprotein complex dysfunction: a regulatory link between muscular dystrophy and cancer cachexia. *Cancer Cell* 8(5):421-432.

Adams C M, et al. (2011) Altered mRNA expression after long-term soleus electrical stimulation training in humans with paralysis. *Muscle & nerve* 43(1):65-75.

Adams G R & Haddad F (1996) The relationships among IGF-1, DNA content, and protein accumulation during skeletal muscle hypertrophy. *J Appl Physiol* 81(6):2509-2516.

Adams G R, et al. (1999) Time course of changes in markers of myogenesis in overloaded rat skeletal muscles. *J Appl Physiol* 87(5): 1705-1712.

Adams V, et al. (2008) Induction of MuRF1 is essential for TNF-alpha-induced loss of muscle function in mice. *Journal of molecular biology* 384(1):48-59.

Barton-Davis E R, et al. (1998) Viral mediated expression of insulin-like growth factor I blocks the aging-related loss of skeletal muscle function. *Proceedings of the National Academy of Sciences of the United States of America* 95(26): 15603-15607.

Baumgartner, R. N., Koehler, K. M., Gallagher, D., Romero, L., Heymsfield, S. B., Ross, R. R., Garry, P. J., and Lindeman, R. D. (1998) *Am J Epidemiol* 147, 755-763

Bennani-Baiti N & Walsh D (2011) Animal models of the cancer anorexia-cachexia syndrome. *Support Care Cancer* 19(9):1451-1463.

Bodine S C, et al. (2001) Akt/mTOR pathway is a crucial regulator of skeletal muscle hypertrophy and can prevent muscle atrophy in vivo. *Nat Cell Biol* 3(11): 1014-1019.

Bodine S C, et al. (2001) Identification of ubiquitin ligases required for skeletal muscle atrophy. Science (New York, N.Y. 294(5547):1704-1708.

Burridge S (2011) Obesity and diabetes: lipid boosts muscle and shrinks fat. *Nature reviews. Drug discovery* 10(8): 576.

Burton, L. A., and Sumukadas, D. (2010) *Clin Interv Aging* 5, 217-228

Busquets S, et al. (2012) Myostatin blockage using actRIIB antagonism in mice bearing the Lewis lung carcinoma results in the improvement of muscle wasting and physical performance. *Journal of cachexia, sarcopenia and muscle* 3(1):37-43.

Chiu F L & Lin J K (2008) Tomatidine inhibits iNOS and COX-2 through suppression of N F-kappaB and JNK pathways in LPS-stimulated mouse macrophages. *FEBS letters* 582(16):2407-2412.

Choi S H, et al. (2012) Structure-activity relationships of alpha-, beta(1)-, gamma-, and delta-tomatine and tomatidine against human breast (MDA-MB-231), gastric (KATO-III), and prostate (PC3) cancer cells. *Journal of agricultural and food chemistry* 60(15):3891-3899.

Cohen S, et al. (2009) During muscle atrophy, thick, but not thin, filament components are degraded by MuRF1-dependent ubiquitylation. *The Journal of cell biology* 185(6):1083-1095.

Coker, R. H., and Wolfe, R. R. (2011) *Curr Opin Clin Nutr Metab Care* 15, 7-11

Cornelissen B, McLarty K, Kersemans V, & Reilly R M (2008) The level of insulin growth factor-1 receptor expression is directly correlated with the tumor uptake of (111)In-IGF-1(E3R) in vivo and the clonogenic survival of breast cancer cells exposed in vitro to trastuzumab (Herceptin). *Nuclear medicine and biology* 35(6):645-653.

Coss C C, Bohl C E, & Dalton J T (2011) Cancer cachexia therapy: a key weapon in the fight against cancer. *Curr Opin Clin Nutr Metab Care* 14(3):268-273.

Das S K, et al. (2011) Adipose triglyceride lipase contributes to cancer-associated cachexia. *Science* (New York, N.Y. 333(6039):233-238.

De Angel R E, Smith S M, Glickman R D, Perkins S N, & Hursting S D (2010) Antitumor effects of ursolic acid in a mouse model of postmenopausal breast cancer. *Nutrition and cancer* 62(8): 1074-1086.

de Melo C L, et al. (2010) Oleanolic acid, a natural triterpenoid improves blood glucose tolerance in normal mice and ameliorates visceral obesity in mice fed a high-fat diet. *Chem Biol Interact* 185(1):59-65.

Delibegovic M, et al. (2007) Improved glucose homeostasis in mice with muscle-specific deletion of protein-tyrosine phosphatase 1B. *Molecular and cellular biology* 27(21): 7727-7734.

Dobrowolny G, et al. (2005) Muscle expression of a local Igf-1 isoform protects motor neurons in an ALS mouse model. *The Journal of cell biology* 168(2): 193-199.

Doucet M, et al. (2007) Muscle atrophy and hypertrophy signaling in patients with chronic obstructive pulmonary disease. *American journal of respiratory and critical care medicine* 176(3):261-269.

Dubowitz V, et al. (2007) *Muscle biopsy: a practical approach* (Saunders Elsevier, Philadelphia) 3rd Ed pp XIII, 611 s.

Dupont J, et al. (2001) Insulin-like growth factor 1 (IGF-1)-induced twist expression is involved in the anti-apoptotic effects of the IGF-1 receptor. *The Journal of biological chemistry* 276(28):26699-26707.

Ebert S M, et al. (2010) The transcription factor ATF4 promotes skeletal myofiber atrophy during fasting. *Molecular endocrinology* 24(4):790-799.

Ebert S M, et al. (2012) Stress-induced skeletal muscle Gadd 45a expression reprograms myonuclei and causes muscle atrophy. *The Journal of biological chemistry.*

Edwards, M. G., Anderson, R. M., Yuan, M., Kendziorski, C. M., Weindruch, R., and Prolla, T. A. (2007) *BMC genomics* 8, 80

Fearon K C (2011) Cancer cachexia and fat-muscle physiology. *The New England journal of medicine* 365(6):565-567.

Flood, M., and Newman, A. M. (2007) *Journal of gerontological nursing* 33, 19-35; quiz 36-17

Frighetto R T S, et al. (2008) Isolation of ursolic acid from apple peels by high speed counter-current chromatography. *Food Chemistry* 106:767-771.

Frost R A, et al. (2009) Regulation of REDD1 by insulin-like growth factor-I in skeletal muscle and myotubes. *J Cell Biochem* 108(5):1192-1202.

Gentile M A, et al. (2010) Androgen-mediated improvement of body composition and muscle function involves a novel early transcriptional program including IGF 1, mechano growth factor, and induction of {beta}-catenin. *Journal of molecular endocrinology* 44(1):55-73.

Glass D J (2005) Skeletal muscle hypertrophy and atrophy signaling pathways. *The international journal of biochemistry & cell biology* 37(10): 1974-1984.

Goldstein B J, et al. (2000) Tyrosine dephosphorylation and deactivation of insulin receptor substrate-1 by protein-tyrosine phosphatase 1B. Possible facilitation by the formation of a ternary complex with the Grb2 adaptor protein. *The Journal of biological chemistry* 275(6):4283-4289.

Hameed M, et al. (2004) The effect of recombinant human growth hormone and resistance training on IGF-I mRNA expression in the muscles of elderly men. *The Journal of physiology* 555(Pt 1):231-240.

Hirose M, et al. (2001) Long-term denervation impairs insulin receptor substrate-1-mediated insulin signaling in skeletal muscle. *Metabolism: clinical and experimental* 50(2):216-222.

Hishiya A, et al. (2006) A novel ubiquitin-binding protein ZNF216 functioning in muscle atrophy. *The EMBO journal* 25(3):554-564.

Hu Z, et al. (2009) Endogenous glucocorticoids and impaired insulin signaling are both required to stimulate muscle wasting under pathophysiological conditions in mice. *The Journal of clinical investigation* 119(10):3059-3069.

Izumiya Y, et al. (2008) Fast/Glycolytic muscle fiber growth reduces fat mass and improves metabolic parameters in obese mice. *Cell metabolism* 7(2):159-172.

Jagoe R T, et al. (2002) Patterns of gene expression in atrophying skeletal muscles: response to food deprivation. *Faseb J* 16(13): 1697-1712.

Jang S M, et al. (2009) Ursolic acid enhances the cellular immune system and pancreatic beta-cell function in streptozotocin-induced diabetic mice fed a high-fat diet. *Int Immunopharmacol* 9(1): 113-119.

Janssen, I., Shepard, D. S., Katzmarzyk, P. T., and Roubenoff, R. (2004) *J Am Geriatr Soc* 52, 80-85

Jayaprakasam B, et al. (2006) Amelioration of obesity and glucose intolerance in high-fat-fed C57B L/6 mice by anthocyanins and ursolic acid in Cornelian cherry (Cornus mas). *J Agric Food Chem* 54(1):243-248.

Jung S H, et al. (2007) Insulin-mimetic and insulin-sensitizing activities of a pentacyclic triterpenoid insulin receptor activator. *The Biochemical journal* 403(2):243-250.

Kajimura S, Seale P, & Spiegelman B M (2010) Transcriptional control of brown fat development. *Cell metabolism* 11(4):257-262.

Kandarian S C & Jackman R W (2006) Intracellular signaling during skeletal muscle atrophy. *Muscle & nerve* 33(2):155-165.

Klaman L D, et al. (2000) Increased energy expenditure, decreased adiposity, and tissue-specific insulin sensitivity in protein-tyrosine phosphatase 1B-deficient mice. *Molecular and cellular biology* 20(15):5479-5489.

Koh S J, et al. (2012) Sensitization of ionizing radiation-induced apoptosis by ursolic acid. *Free radical research* 46(3):339-345.

Kunkel S D, et al. (2011) mRNA Expression Signatures of Human Skeletal Muscle Atrophy Identify a Natural Compound that Increases Muscle Mass. *Cell metabolism* 13(6):627-638.

Kunkel S D, et al. (2012) Ursolic Acid increases skeletal muscle and brown fat and decreases diet-induced obesity, glucose intolerance and Fatty liver disease. *PloS one* 7(6):e39332.

Kwon S H, et al. (2010) Apoptotic action of ursolic acid isolated from Corni fructus in RC-58T/h/SA #4 primary human prostate cancer cells. *Bioorganic & medicinal chemistry letters* 20(22):6435-6438.

Lagirand-Cantaloube J, et al. (2008) The initiation factor eIF3-f is a major target for atroginl/MAFbx function in skeletal muscle atrophy. *The EMBO journal* 27(8): 1266-1276.

Lai K M, et al. (2004) Conditional activation of akt in adult skeletal muscle induces rapid hypertrophy. *Molecular and cellular biology* 24(21):9295-9304.

Lamb J, et al. (2006) The Connectivity Map: using gene-expression signatures to connect small molecules, genes, and disease. *Science* (New York, N.Y. 313(5795):1929-1935.

Lauthier, F., Taillet, L., Trouillas, P., Delage, C., and Simon, A. (2000) Ursolic acid triggers calcium-dependent apoptosis in human Daudi cells. *Anti-cancer drugs* 11, 737-745

Lecker S H, et al. (2004) Multiple types of skeletal muscle atrophy involve a common program of changes in gene expression. *Faseb J* 18(1):39-51.

Lee S J (2004) Regulation of muscle mass by myostatin. *Annu Rev Cell Dev Biol* 20:61-86.

Leger B, et al. (2006) Human skeletal muscle atrophy in amyotrophic lateral sclerosis reveals a reduction in Akt and an increase in atrogin-1. *Faseb J* 20(3):583-585.

Levine S, et al. (2008) Rapid disuse atrophy of diaphragm fibers in mechanically ventilated humans. *The New England journal of medicine* 358(13): 1327-1335.

Liu J (1995) Pharmacology of oleanolic acid and ursolic acid. *Journal of ethnopharmacology* 49(2): 57-68.

Liu J (2005) Oleanolic acid and ursolic acid: research perspectives. *Journal of ethnopharmacology* 100(1-2):92-94.

Lonning P E & Helle S I (2004) IGF-1 and breast cancer. *Novartis Foundation symposium* 262:205-212; discussion 212-204, 265-208.

Ma J, et al. (1999) Prospective study of colorectal cancer risk in men and plasma levels of insulin-like growth factor (IGF)-I and IGF-binding protein-3. *Journal of the National Cancer Institute* 91(7):620-625.

Mammucari C, et al. (2007) FoxO3 controls autophagy in skeletal muscle in vivo. *Cell metabolism* 6(6):458-471.

Miller, R. A., and Nadon, N. L. (2000) *The journals of gerontology* 55, B 117-123

Musarò A, et al. (2001) Localized Igf-1 transgene expression sustains hypertrophy and regeneration in senescent skeletal muscle. *Nature Genetics* 27(2):195-200.

Nathanson L, Meelu M A, & Losada R (1994) Chemohormone therapy of metastatic melanoma with megestrol acetate plus dacarbazine, carmustine, and cisplatin. *Cancer* 73(1):98-102.

Novotny L, Vachalkova A, & Biggs D (2001) Ursolic acid: an anti-tumorigenic and chemopreventive activity. Mini-review. *Neoplasma* 48(4):241-246.

Pallafacchina G, et al. (2002) A protein kinase B-dependent and rapamycin-sensitive pathway controls skeletal muscle growth but not fiber type specification. *Proceedings of the National Academy of Sciences of the United States of America* 99(14):9213-9218.

Prasad S, et al. (2012) Ursolic Acid Inhibits Growth and Metastasis of Human Colorectal Cancer in an Orthotopic Nude Mouse Model by Targeting Multiple Cell Signaling Pathways: Chemosensitization with Capecitabine. *Clin Cancer Res.*

Qian S, et al. (2010) Synthesis and biological evaluation of oleanolic acid derivatives as inhibitors of protein tyrosine phosphatase 1B. *J Nat Prod* 73(11):1743-1750.

Reagan-Shaw S, Nihal M, & Ahmad N (2008) Dose translation from animal to human studies revisited. *Faseb J* 22(3):659-661.

Sacheck J M, et al. (2004) IGF-I stimulates muscle growth by suppressing protein breakdown and expression of atrophy-related ubiquitin ligases, atrogin-1 and MuRF1. *Am J Physiol Endocrinol Metab* 287(4):E591-601.

Sacheck J M, et al. (2007) Rapid disuse and denervation atrophy involve transcriptional changes similar to those of muscle wasting during systemic diseases. *Faseb J* 21(1): 140-155.

Sakuma K & Yamaguchi A (2012) Novel intriguing strategies attenuating to sarcopenia. *Journal of aging research* 2012:251217.

Sandri M (2008) Signaling in muscle atrophy and hypertrophy. *Physiology* (Bethesda) 23:160-170.

Sandri M, et al. (2004) Foxo transcription factors induce the atrophy-related ubiquitin ligase atrogin-1 and cause skeletal muscle atrophy. *Cell* 117(3):399-412.

Sandri M, et al. (2006) PGC-1alpha protects skeletal muscle from atrophy by suppressing FoxO3 action and atrophy-specific gene transcription. *Proceedings of the National Academy of Sciences of the United States of America* 103(44): 16260-16265.

Shanmugam M K, et al. (2011) Ursolic acid inhibits multiple cell survival pathways leading to suppression of growth of prostate cancer xenograft in nude mice. *Journal of molecular medicine* (Berlin, Germany) 89(7):713-727.

Shavlakadze T, et al. (2005) Insulin-like growth factor I slows the rate of denervation induced skeletal muscle atrophy. *Neuromuscul Disord* 15(2):139-146.

Siegel R, Ward E, Brawley O, & Jemal A (2011) Cancer statistics, 2011: the impact of eliminating socioeconomic and racial disparities on premature cancer deaths. *C A Cancer J Clin* 61(4):212-236.

Sivakumar G, et al. (2009) Plant-based corosolic acid: future anti-diabetic drug?*Biotechnol J* 4(12):1704-1711.

Skipworth R J, Stewart G D, Dejong C H, Preston T, & Fearon K C (2007) Pathophysiology of cancer cachexia: much more than host-tumour interaction? *Clinical nutrition* (Edinburgh, Scotland) 26(6):667-676.

Stitt T N, et al. (2004) The IGF-1/PI3K/Akt pathway prevents expression of muscle atrophy-induced ubiquitin ligases by inhibiting FOXO transcription factors. *Mol Cell* 14(3):395-403.

Tan B H & Fearon K C (2008) Cachexia: prevalence and impact in medicine. *Curr Opin Clin Nutr Metab Care* 11(4):400-407.

Tan B H, Birdsell L A, Martin L, Baracos V E, & Fearon K C (2009) Sarcopenia in an overweight or obese patient is an adverse prognostic factor in pancreatic cancer. *Clin Cancer Res* 15(22):6973-6979.

Tureckova J, et al. (2001) Insulin-like growth factor-mediated muscle differentiation: collaboration between phosphatidylinositol 3-kinase-Akt-signaling pathways and myogenin. *The Journal of biological chemistry* 276(42): 39264-39270.

von Haehling S & Anker S D (2010) Cachexia as a major underestimated and unmet medical need: facts and numbers. *Journal of cachexia, sarcopenia and muscle* 1(1): 1-5.

Wang X, et al. (2011) Ursolic acid inhibits proliferation and induces apoptosis of cancer cells in vitro and in vivo. *Journal of biomedicine & biotechnology* 2011:419343.

Wang Z H, et al. (2010) Anti-glycative effects of oleanolic acid and ursolic acid in kidney of diabetic mice. *European journal of pharmacology* 628(1-3):255-260.

Wang, J. S., Ren, T. N., and Xi, T. (2010) *Medical oncology* 29, 10-15

Welle, S., Brooks, A. I., Delehanty, J. M., Needler, N., Bhatt, K., Shah, B., and Thornton, C. A. (2004) *Experimental gerontology* 39, 369-377

Wenz T, et al. (2009) Increased muscle PGC-1alpha expression protects from sarcopenia and metabolic disease during aging. *Proceedings of the National Academy of Sciences of the United States of America* 106(48):20405-20410.

Yakar S, et al. (1999) Normal growth and development in the absence of hepatic insulin-like growth factor I. *Proceedings of the National Academy of Sciences of the United States of America* 96(13):7324-7329.

Zabolotny J M, et al. (2004) Transgenic overexpression of protein-tyrosine phosphatase 1B in muscle causes insulin resistance, but overexpression with leukocyte antigen-related phosphatase does not additively impair insulin action. *The Journal of biological chemistry* 279(23): 24844-24851.

Zhang W, et al. (2006) Ursolic acid and its derivative inhibit protein tyrosine phosphatase 1B, enhancing insulin receptor phosphorylation and stimulating glucose uptake. *Biochimica et biophysica acta* 1760(10): 1505-1512.

Zhang Y N, et al. (2008) Oleanolic acid and its derivatives: new inhibitor of protein tyrosine phosphatase 1B with cellular activities. *Bioorg Med Chem* 16(18):8697-8705.

Zhou X, et al. (2010) Reversal of cancer cachexia and muscle wasting by ActRIIB antagonism leads to prolonged survival. *Cell* 142(4):531-43.

What is claimed is:

1. A method of:
increasing muscle quality;
increasing muscle specific force;
increasing muscle strength;
increasing exercise capacity;
modulating muscle health;
increasing muscle force generation;
reducing obesity;
treating a muscle disorder;
promoting muscle health;
promoting normal muscle function; or
promoting healthy aging in an animal comprising administering to an animal in need thereof a composition comprising not less than 0.05% by weight of a compound selected from the group consisting of α-tomatine and a compound having a structure represented by a formula:

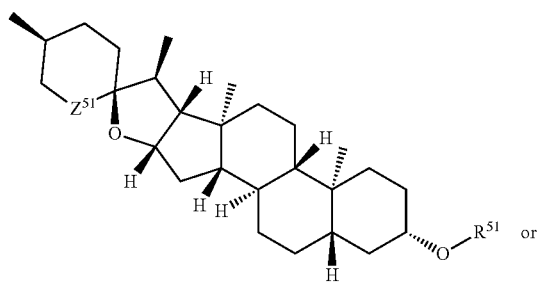

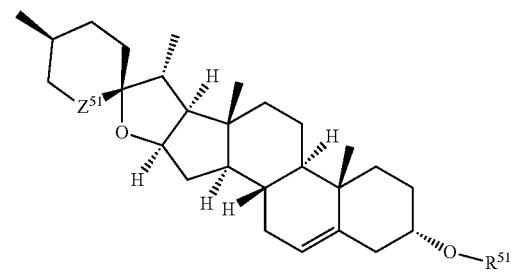

wherein $R^{51}$ is selected from H, $C_1$-$C_6$ alkyl, and $COR^{53}$;

$R^{53}$ is $C_1$-$C_6$ alkyl;

$Z^{51}$ is $NR^{54}$; and $R^{54}$ is selected from H and $C_1$-$C_6$ alkyl, or pharmaceutically acceptable salt thereof.

2. The method according to claim 1, wherein the compound is a compound having a structure represented by the formula E1

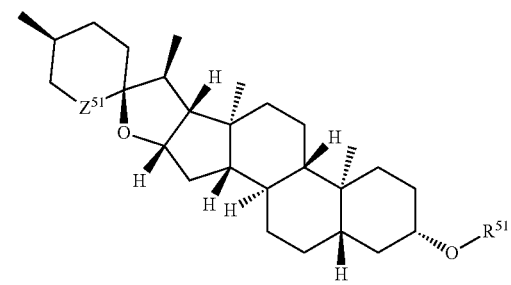

or pharmaceutically acceptable salt thereof.

3. The method according to claim 2, wherein $R^{51}$ is H and $R^{54}$ is H.

4. The method according to claim 2, wherein the compound is a compound having the structure represented by formula:

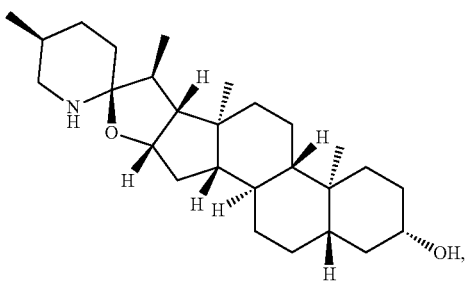 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

or pharmaceutically acceptable salt thereof.

5. The method according to claim 1 for treating a muscle disorder, wherein the muscle disorder is sarcopenia, and wherein the compound is α-tomatine; or a compound having a structure represented by the formula:

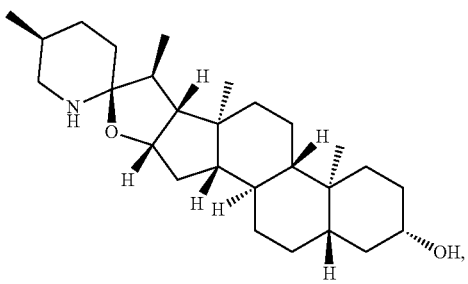 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

or a pharmaceutically acceptable salt thereof.

6. The method according to claim 1, wherein said composition comprises not less than 0.14% by weight of said compound or pharmaceutically acceptable salt thereof.

7. The method according to claim 1, wherein said composition comprises not less than 0.28% by weight of said compound or pharmaceutically acceptable salt thereof.

8. The method according to claim 2, wherein the compound or pharmaceutically acceptable salt thereof is present in an amount greater than 5 mg.

9. The method according to claim 1, wherein the composition is a solution, dispersion, suspension or emulsion.

10. The method according to claim 1, wherein said composition is animal chow.

11. The method according to claim 10, wherein the compound is α-tomatine.

12. The method according to claim 1, comprising administering the composition orally, and wherein the composition comprises a preservative.

13. The method according to claim 12, wherein the composition is animal chow.

14. The method according to claim 13, wherein the animal chow additionally comprises at least one further additive selected from the group consisting of flavoring agents, coloring agents, and binders.

15. A method of:

increasing muscle quality;
increasing muscle specific force;
increasing muscle strength;
increasing exercise capacity;
modulating muscle health;
increasing muscle force generation;
reducing obesity;
treating a muscle disorder;
promoting muscle health;
promoting normal muscle function; or
promoting healthy aging in an animal in need thereof, the method comprising administering to the animal in need thereof a composition selected from a nutraceutical, animal chow, medicinal food, energy bar, energy drink, sports drink, protein bar, tea, coffee, milk, milk product, cereal, oatmeal, infant formula, and supplement, wherein said composition provides not less than 0.05% by weight of a compound selected from the group consisting of α-tomatine and a compound having a structure represented by a formula:

E1

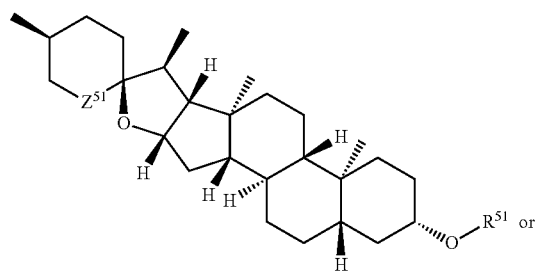

E2

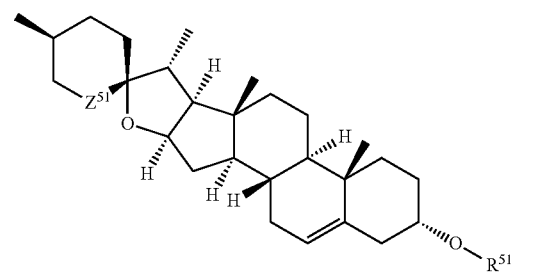

wherein $R^{51}$ is selected from H, $C_1$-$C_6$ alkyl, and $COR^{53}$;

$R^{53}$ is $C_1$-$C_6$ alkyl;

$Z^{51}$ is $NR^{54}$; and $R^{54}$ is selected from H and $C_1$-$C_6$ alkyl, or a pharmaceutically acceptable salt thereof.

16. The method according to claim 15, comprising administering the composition so as to provide to the animal 0.1 to 250 mg/kg per day of the compound or pharmaceutically acceptable salt thereof.

17. The method according to claim 15, comprising administering the composition so as to provide to the animal 0.5 to 100 mg/kg per day of the compound or pharmaceutically acceptable salt thereof.

18. The method according to claim 15, comprising administering the composition so as to provide to the animal 5.0 to 100 mg/kg per day of the compound or pharmaceutically acceptable salt thereof.

19. The method according claim 18, comprising administering the composition so as to provide to the animal greater than 50 mg per day of the compound or pharmaceutically acceptable salt thereof.

20. The method according to claim 19, comprising administering the composition orally, wherein the composition comprises at least one further additive selected from the group consisting of preservatives, flavoring agents, coloring agents, and binders, and wherein the compound is a compound having a structure represented by the formula E1 or a pharmaceutically acceptable salt thereof.

21. The method according to claim 1, wherein the compound is α-tomatine or a pharmaceutically acceptable salt thereof.

22. The method according to claim 1, wherein the composition is a capsule or tablet.

23. The method according to claim 1, wherein the animal is a non-human primate, horse, pig, rabbit, dog, sheep, goat, cow, cat, guinea pig, fish, or bird, and wherein the compound is selected from:
   α-tomatine; and
   a compound having a structure represented by a formula:

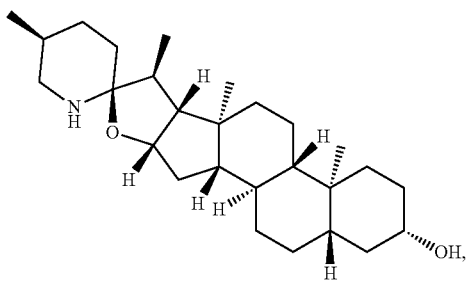 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

or a pharmaceutically acceptable salt thereof.

24. The method according to claim 15, wherein the animal is a non-human primate, horse, pig, rabbit, dog, sheep, goat, cow, cat, guinea pig, fish, or bird, wherein the composition is a nutraceutical, animal chow, medicinal food, or supplement, and wherein said composition provides a compound selected from the group consisting of α-tomatine and a compound and wherein the compound is selected from:
   α-tomatine; and
   a compound having a structure represented by a formula:

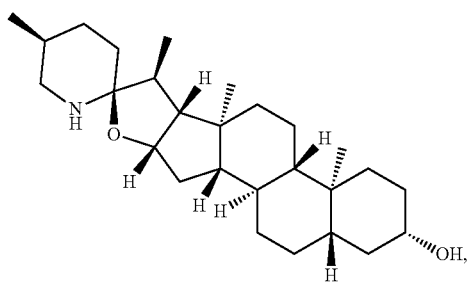 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

or a pharmaceutically acceptable salt thereof.

25. The method according to claim 15, wherein the composition provides greater than 5 mg of the compound or pharmaceutically acceptable salt thereof.

* * * * *